(12) United States Patent
Hasserodt et al.

(10) Patent No.: US 10,179,929 B2
(45) Date of Patent: Jan. 15, 2019

(54) WATER-SOLUBLE ACTIVATABLE MOLECULAR PROBES, INTERMEDIATES FOR THE SYNTHESIS THEREOF AND ASSOCIATED DETECTION METHODS

(71) Applicants: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR)

(72) Inventors: Jens Hasserodt, Lyons (FR); Maxime Prost, Lyons (FR)

(73) Assignees: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/320,448

(22) PCT Filed: Jun. 24, 2015

(86) PCT No.: PCT/FR2015/051705
§ 371 (c)(1),
(2) Date: Dec. 20, 2016

(87) PCT Pub. No.: WO2015/197981
PCT Pub. Date: Dec. 30, 2015

(65) Prior Publication Data
US 2017/0159100 A1 Jun. 8, 2017

(30) Foreign Application Priority Data
Jun. 26, 2014 (FR) ..................... 14 56014

(51) Int. Cl.
| A61K 49/00 | (2006.01) |
| C12Q 1/34 | (2006.01) |
| C12Q 1/44 | (2006.01) |
| C07D 403/12 | (2006.01) |
| C07D 405/14 | (2006.01) |
| C07D 403/08 | (2006.01) |
| C07D 405/12 | (2006.01) |
| C07D 241/04 | (2006.01) |
| C07D 403/14 | (2006.01) |

(52) U.S. Cl.
CPC ............ *C12Q 1/34* (2013.01); *A61K 49/0021* (2013.01); *A61K 49/0052* (2013.01); *C07D 241/04* (2013.01); *C07D 403/08* (2013.01); *C07D 403/12* (2013.01); *C07D 403/14* (2013.01); *C07D 405/12* (2013.01); *C07D 405/14* (2013.01); *C12Q 1/44* (2013.01); *C12Y 301/01003* (2013.01); *C12Y 305/01011* (2013.01)

(58) Field of Classification Search
CPC .. C07D 403/14; C07D 405/12; C07D 405/14; C12Q 1/34; C12Q 1/44; C12Y 301/01003; C12Y 305/01011
See application file for complete search history.

(56) References Cited

FOREIGN PATENT DOCUMENTS

| WO | 00/59510 A1 | 10/2000 | |
| WO | 2007/146066 A2 | 12/2007 | |
| WO | WO 2007/146066 | * 12/2007 | ........... C07D 241/04 |
| WO | 2012/122420 A2 | 9/2012 | |

(Continued)

OTHER PUBLICATIONS

West, Anthony R., Solid State Chemistry and Its Applications, Wiley, New York, 1988, 358.*
International Search Report dated Nov. 18, 2015 for Application No. PCT/FR2015/051705.
Prost, Maxime, "Sondes Moleculaires Comprenant des Espaceurs Auto-Effondrables Multifonctionnels pour la Detection D'activites Enzymatiques", Ecole Normale Supérieure de Lyon, Jul. 3, 2014, 2 pages.
Huang, Z., et al., "2-(2'-Phosphoryloxyphenyl)-4(3H)-quinazolinone Derivatives as Fluorogenic Precipitating Substrates of Phosphatases", Analytical Biochemistry, vol. 207, 1992, pp. 32-39.

(Continued)

*Primary Examiner* — Erich A Leeser
(74) *Attorney, Agent, or Firm* — Ladas & Parry LLP; Malcolm J. MacDonald

(57) ABSTRACT

The invention provides probes with formula (I):

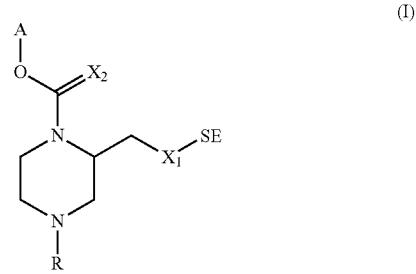

Figure 1:
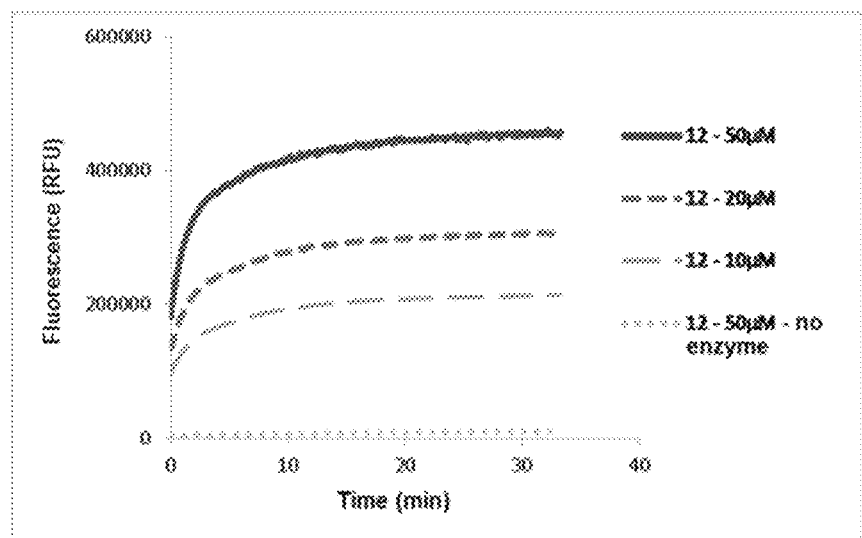

in which:
$X_1$=NH, O, or S; $X_2$=O or S; SE is a labile group, which may be eliminated under the action of a stimulus that may in particular be the presence of an enzyme, a chemical compound, or a physicochemical characteristic of the medium in which the probe is located; A is an aromatic group that, following cleavage of the C($X_2$)—O bond in aqueous solution, leads to the liberation of a chromophore or a fluorophore, R represents a hydrogen atom or -(L)n-GP, in which n is equal to 0 or 1, L is a linker arm, and GP is a hydrosolubilizing group;
as well as their physiologically acceptable salts, solvates, or hydrates. The invention also provides intermediates for the synthesis thereof and detection methods employing them.

13 Claims, 4 Drawing Sheets

(56) References Cited

FOREIGN PATENT DOCUMENTS

| WO | 2013/045854 A1 | 4/2013 |
|---|---|---|
| WO | 2014/020285 A1 | 2/2014 |

OTHER PUBLICATIONS

Shi, H., et al., "Real-Time Monitoring of Cell Apoptosis and Drug Screening Using Fluorescent Light-Up Probe with Aggregation-Induced Emission Characteristics", J. Am. Chem. Soc., vol. 134, 2012, pp. 17972-17981.

Ho, Nan-hui, et al., "Development of water-soluble far-red fluorogenic dyes for enzyme sensing", Tetrahedron, vol. 62, 2006, pp. 578-585.

Karton-Lifshin, N., et al., "A Unique Paradigm for a Turn-ON Near-Infrared Cyanine-Based Probe: Noninvasive Intravital Optical Imaging of Hydrogen Peroxide", J. Am. Chem. Soc., vol. 133, 2011, pp. 10960-10965.

Sagi, A., et al., "Self-Immolative Polymers", J. Am. Chem. Soc., vol. 130, 2008, pp. 5434-5435.

Danieli, E., et al., "Molecular probe for enzymatic activity with dual output", Bioorg. Med. Chem., vol. 15, 2007, pp. 7318-7324.

Rokita, S., "Reversible Alkylation of DNA by Quinone Methides", Quinone Methides, 2009, pp. 297-327.

Thompson, D., et al., "o-Methoxy-4-alkylphenols That Form Quinone Methides of Intermediate Reactivity Are the Most Toxic in Rat Liver Slices", Chem. Res. Toxicol., vol. 8, No. 3, 1995, pp. 323-327.

McCracken, P., et al., "Covalent Modification of Proteins and Peptides by the Quinone Methide from 2-tert-Butyl-4,6-dimethylphenol: Selectivity and Reactivity with Respect to Competitive Hydration", J. Org. Chem., vol. 62, 1997, pp. 1820-1825.

Jin, Hui-juan, et al., "Development of a new enzyme-responsive self-immolative spacer conjugate applicable to the controlled drug release", Bioorg. Med. Chem., vol. 20, 2012, pp. 3465-3469.

Meyer, Y., et al., "Development of a New Nonpeptidic Self-Immolative Spacer. Application to the Design of Protease Sensing Fluorogenic Probes", Org. Lett. vol. 10, No. 8, 2008, pp. 1517-1520.

Gopin, A., et al., "Enzymatic Activation of Second-Generation Dendritic Prodrugs: Conjugation of Self-Immolative Dendrimers with Poly(ethylene glycol) via Click Chemistry", Bioconjugate Chem., vol. 17, 2006, pp. 1432-1440.

Karton-Lifshin, N., et al., "'Donor-Two-Acceptor' Dye Design: A Distinct Gateway to NIR Fluorescence", J. Am. Chem. Soc., vol. 134, 2012, pp. 20412-20420.

Barker, G., et al, "Diamine-Free Lithiation—Trapping of N-Boc Heterocycles using s-BuLi in THF", Org. Lett., vol. 12, No. 18, pp. 4176-4179.

* cited by examiner

WATER-SOLUBLE ACTIVATABLE MOLECULAR PROBES, INTERMEDIATES FOR THE SYNTHESIS THEREOF AND ASSOCIATED DETECTION METHODS

The invention relates to activatable molecular probes for use in the field of diagnostics, incorporating a linker arm that self-immolates in response to a stimulus that may in particular be the presence of an enzyme, a chemical compound, or a physicochemical characteristic of the environment of the probe, in order to liberate a detectable entity of the fluorophore or chromophore type.

Detecting an enzymatic activity may be of great use in the analysis of a biological or chemical sample. Whole organisms, cells or cell extracts, biological liquids, or chemical mixtures are examples of biological or chemical samples in which an enzymatic activity may be detected. Many biomarkers of a variety of diseases are constituted by enzymes. They are also involved in numerous cell processes and therefore have been the focus of innumerable studies by cell biologists. Thus, their detection can provide information regarding a particular metabolic or morbid condition, for example. For this reason, probes that are capable of detecting an enzymatic activity are highly useful and have been the focus of a great many studies.

In particular, the work of one of the inventors of the present patent application may be mentioned, corresponding to application WO 2013/045854, which concerns peptidase substrates, and application WO 2014/020285, which concerns glycosidase substrates, both of which use a self-immolative linker bonding a substrate of the enzyme of interest to an aryl group that, following cleavage of the substrate, results in cyclization of the linker and the release of an Excited State Intramolecular Proton Transfer (ESIPT) fluorophore.

However, good solubility in water of the molecular probes responding to an enzymatic activity is one of the essential criteria in ensuring that the results they provide are reliable. Specifically, adding an organic co-solvent in order to dissolve a hydrophobic molecule generally substantially reduces the activity of the enzymes. In addition, although the use of low concentrations of solutions is acceptable for some in vitro tests, the transition to cellular incubation or systemic injections in vivo requires the use of solutions with much higher concentrations because they become diluted to a great extent once injected. Furthermore, a co solvent cannot be used in vivo. Finally, a molecule that is too hydrophobic runs the risk of accumulating in the adipose tissues and not in the target tissues.

Chemists have therefore been concerned with the problem of solubility for a long time, and a number of solutions have been developed. The first was to incorporate groups with a saline character as enzymatic substrates. That solution, as encountered in phosphatase probes (Haugland et al. Anal. Biochem. 1992, 207, 32) or caspase-3 probes (Liu et al. J. Am. Chem. Soc. 2012, 134, 17972), for example, functions very well, but it limits the envisaged choice of enzymes, since those that recognize apolar substrates cannot be targeted. In addition, molecules with negative charges pass through the cell membrane with difficulty, thereby limiting the application to targeting extracellular enzymes. A second solution is to graft hydrosolubilizing groups onto the signalophore used, often sulfonate groups (Tung et al. Tetrahedron 2006, 62, 578; Shabat et al. J. Am. Chem. Soc. 2011, 133, 10960). Here again, the hydrosolubilization provided by these motifs is excellent, but this measure is less attractive because it runs the risk of reducing the performance of the signalophore once released from the initial probe following an enzymatic activity. In addition, a solution of that type simply cannot be envisaged when solid state signalophores are to be used. Those two possibilities therefore cannot be generalized to the larger number of molecular probes responding to an enzymatic activity.

Currently, only very few systems exist that can provide a versatile association of a hydrosolubilizing species with an enzymatic substrate with the aim of releasing an optically active molecule. These are generally based on a substituted eliminating linker (Shabat et al. J. Am. Chem. Soc. 2008, 130, 5434) or on a combination of a cyclizing linker and eliminating linkers (Shabat et al. Bioorg. Med. Chem. 2007, 15, 7318). The problem is that substituted eliminating linkers are known to produce reaction intermediates that are highly toxic (Rokita, Quinone Methides, $1^{st}$ ed. 2009, John Wiley and Sons Inc.; Bolton et al. Chem. Res. Toxicol. 1995, 8, 323; Thatcher et al. J. Org. Chem. 1997, 62, 1820). What is more, the cyclization/elimination combination is far from ideal because it introduces a great deal of complexity (two linkers in series have to be used), while demonstrating immolation kinetics that are far from being satisfactory (Wu et al. Bioorg. Med. Chem. 2012, 20, 3465), or indeed an instability in the face of spontaneous hydrolysis that is not negligible (Romieu et al Org. Lett. 2008, 10, 1517). Certain constructs deliver their active molecule over several tens of hours (Shabat et al. Bioconjugate Chem. 2006, 17, 1432), which makes them difficult to use in rapidly detecting the presence or absence of certain analytes in a given sample.

Thus, it would be desirable to develop a new generation of cyclizing linkers that can be used to incorporate any enzymatic substrate, irrespective of whether it is polar or apolar, in a manner that is versatile and satisfies the requirements for solubility. However, this linker must retain rapid immolation kinetics and must allow for efficient enzymatic recognition.

In the context of the invention, the inventors propose a novel generation of probes that both offer satisfactory solubility in water, and also are easy to synthesize and modify because of the presence of a piperazine group in which one of the nitrogen atoms could carry a variety of hydrosolubilizing groups. The inventors have elected to propose a solution that incorporates a hydrosolubilizing portion on a third component of the probe, namely in a linker connecting the signalophore and the substrate, which means that any desired enzymatic substrate and any desired reporter molecule can be selected.

The probes in accordance with the invention have the formula (I):

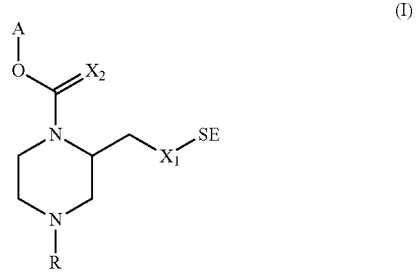

in which:
$X_1$=NH, O, or S;
$X_2$=O or S;

SE is a labile group, and in particular an enzymatic substrate;

A is an aromatic group that, after cleavage of the C(X$_2$)—O bond in aqueous solution, leads to the liberation of a chromophore or a fluorophore;

R represents a hydrogen atom or -(L)n-GP, with n equal to 0 or 1;

L is a linker arm; and

GP is a hydrosolubilizing group;

as well as their physiologically acceptable salts, solvates, or hydrates.

The present invention can be employed to detect a chemical or enzymatic analyte that is capable of cleaving the X$_1$-SE bond by detecting the chromophore or fluorophore that is liberated following cyclization of the piperazinyl type linker with formula:

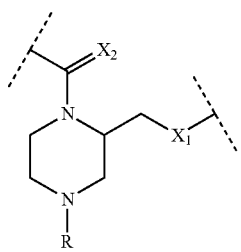

The substrate in accordance with the invention acts as a molecular probe that is capable of revealing the presence of a stimulus such as an enzyme, a chemical compound, or a physicochemical characteristic of the medium in which the probe is located (in particular a change in pH). When the probe is chemically modified by said stimulus, it fragments by means of a cascade reaction in order to liberate a detectable chromophore or fluorophore. It is also possible for the group A to behave as a chromophore or a fluorophore when it is linked to the remainder of the molecule in the probes with formula (I). With "ratiometric" probes, their spectral properties, and in particular absorbance and/or fluorescence properties, are different from the entity liberated under the action of a stimulus such as an enzyme, a chemical compound, or a physicochemical characteristic of the medium in which the probe is located. Advantageously, but not necessarily, the group A may be selected in a manner such that the probe with formula (I) is not detectable by absorption or emission of light before encountering the stimulus, in particular in the form of a an enzyme, a chemical compound, or a physicochemical characteristic of the medium in which the probe is located (i.e. the probe is said to be "furtive").

The labile group SE is such that its elimination, for example by an enzymatic pathway or consecutive upon a purely chemical action (such as a variation in pH or the presence of a reducing agent) ensures, by intramolecular rearrangement of the self-immolative linker, liberation of the fluorophore or chromophore, in particular in the form A-OH or A-O$^-$, or A'=O (A'=O being a form obtained after rearrangement of A-OH, a tautomeric or polymerized form of A-OH). Cleavage of the SE-X$_1$ bond triggers liberation of the fluorophore or chromophore, in particular as A-OH or A-O$^-$, or A'=O (A'=O being a form obtained after rearrangement of A-OH or A-O$^-$, a tautomeric or polymerized form of A-OH), by cyclization of the linker as illustrated in Scheme 1 below:

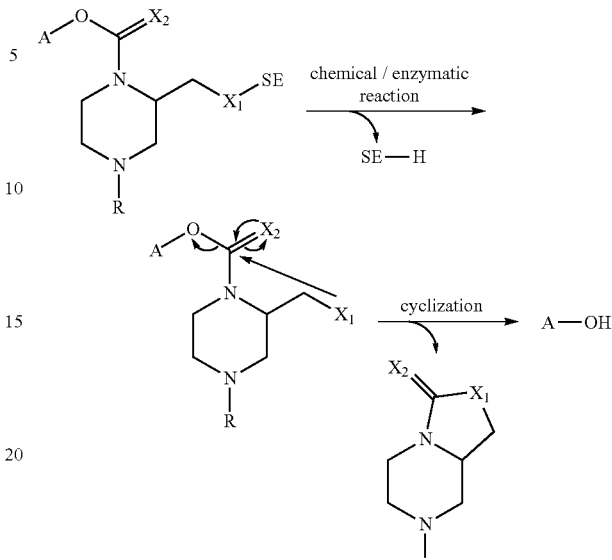

Scheme 1

The probe is composed of four molecular components: i) an intelligent linker that carries, at one end, ii) a labile group SE and, at the other end, iii) an organic group A-O bonded via a carbamate or thiocarbamate group of the linker that, when it is liberated by fragmentation of the linker-A-O conjugate to provide the corresponding enolic or enolate compound, results in the formation of a detectable chromophore or fluorophore, and iv) a hydrosolubilizing group.

In the context of the invention, the presence of the nitrogen atom carrying the group R means that the properties of the probe can be modified and a third functionalization can be introduced alongside the labile group SE and the group A resulting, after elimination of the group SE and cyclization of the linker, in liberation of a detectable chromophore or fluorophore.

In fact, the probes with formula (I) in accordance with the invention comprise a linker of the multifunctionalizable piperazine type that can be used to incorporate a wide choice of enzymatic substrates, and an accompanying group R that, depending on its nature, can be used to render the molecule even more hydrosoluble. The presence of a nitrogen atom means that, starting from the same synthesis intermediate, various hydrosolubilizing functionalizations R can be produced.

In addition, the probes in accordance with the invention have improved solubility compared with their homologs comprising a piperidinyl type linker exemplified in applications WO 2013/045854 and WO 2014/020285 and compared with commercial reagents containing no linker at all, such as 4-methyl-7-(phenylacetamido)coumarin or 4-methylumbelliferyl acetate, for example:

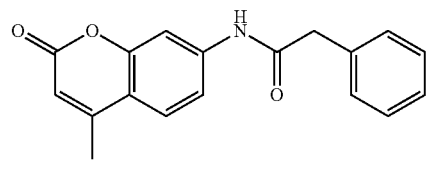

4-methyl-7-(phenylacetamido)coumarine

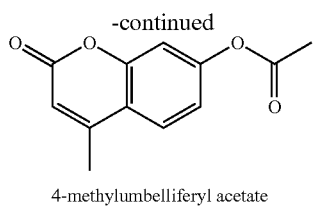

4-methylumbelliferyl acetate

Furthermore, as with applications WO 2013/045854 and WO 2014/020285, the probe comprises a linker that has been pre-organized for cyclization following cleavage of the SE-$X_1$ bond, which accelerates the self-immolation process of the linker while ensuring good enzymatic recognition. However, it was not at all clear that with the modification of the linker carried out in the context of the invention, in which the groups were introduced in order to increase the hydrosolubility, that there was no impact on the reporter activity of the probes. However, in the context of the invention, it has been demonstrated that introducing a charge or increasing the steric hindrance at the group R, and thus at a position close to a site of action of a stimulus (i.e. an enzyme, a chemical compound, or a physicochemical characteristic of the medium in which the probe is located, depending on the nature of the group SE), does not modify the reaction obtained under the action of the corresponding stimulus.

The present invention thus provides compounds with formula (I), irrespective of their variation described in the present patent application, for the in vivo detection, in man or animal, or in vitro, in cellulo or ex vivo detection of a stimulus such as an enzyme, a chemical compound, or a physicochemical characteristic of the medium in which the probe is located, the presence of which causes cleavage of the SE-$X_1$ bond.

In accordance with another aspect, the invention provides an in vitro method of detecting, by means of a probe with formula (I) in accordance with the invention, the presence of a stimulus such as an enzyme, a chemical compound, or a physicochemical characteristic of the medium in which the probe is located, the presence of which causes cleavage of the SE-$X_1$ bond. More precisely, the invention provides a method of detecting the presence of a stimulus such as an enzyme, a chemical compound, or a physicochemical characteristic of the medium in which the probe is located, the presence of which causes cleavage of the SE-$X_1$ bond, comprising the steps of:
  bringing a sample suspected of containing said chemical compound or said enzyme or of having said physicochemical characteristic into contact with a probe with formula (I) in accordance with the invention;
  applying appropriate conditions to permit cleavage of the covalent bond between $X_1$ and SE, under the action of said stimulus, which is followed by a cleavage of the C—O bond between the carbon atom carrying the atom ($X_2$) and the oxygen atom carrying the group A following cyclization of the linker present in the probe with formula (I); and
  quantitative or qualitative analysis of the liberated chromophore or fluorophore.

The sample may be any appropriate biological sample. In particular, it could be a sample of biological fluid, in particular a sample of whole blood, serum, plasma, urine, a tissue sample, or isolated cells, and in particular isolated from a cell medium.

This sample may be used as is or it may have undergone a preparation of the enrichment or culture type well known to the person skilled in the art prior to being brought into the presence of the probe.

Advantageously, the compounds with formula (I) behave as probes functioning in on/off mode, i.e., the probe is "invisible" before cleavage with the stimulus (i.e. an enzyme, a chemical compound, or a variation of a physicochemical characteristic of the medium in which the probe is located, depending on the nature of the group SE). It is also possible to select the group A in a manner such as to obtain different spectral properties between i) the group liberated after cleavage of the C—O bond between the carbon atom carrying the atom ($X_2$) and the oxygen atom carrying the group A, and ii) the probe with formula (I).

In particular, the detection method in accordance with the invention may be carried out under physiological conditions, in particular in an aqueous medium buffered to a pH in the range 4 to 9, and in particular to a pH of the order of 7.4.

In one embodiment of the invention, a fluorophore is liberated and its analysis comprises the following steps:
  exposing the fluorophore to a source of light that is capable of producing light at an absorption wavelength of the fluorophore; and
  detecting the resulting fluorescence.

In another embodiment of the invention, a chromophore is liberated and its analysis comprises the following steps:
  exposing the chromophore to a source of light that is capable of producing light at an absorption wavelength of the chromophore; and
  detecting the light absorbed by the chromophore.

When a chromophore is liberated, a change in color is detected subsequent to the action of the stimulus (i.e. an enzyme, a chemical compound, or a variation in a physicochemical characteristic of the medium in which the probe is located, depending on the nature of the group SE).

Preferably, but not necessarily, the liberated fluorophore or chromophore, in particular in the form A-OH or A-O⁻, or A'=O (A'=O being a form obtained after rearrangement of A-OH or A-O⁻, a tautomeric or polymerized form of A-OH), forms a precipitate in aqueous solution.

The invention is described below in more detail.
Definition of Labile Groups SE

SE is a labile group that can be eliminated in aqueous solution under the action of a stimulus that may in particular be the presence of an enzyme, a chemical compound, or a physicochemical characteristic of the medium in which the probe is located. The SE may in particular be eliminated in an aqueous medium. An example of a physicochemical property that may be mentioned is a variation in pH or varying the redox potential, the latter cleaving the disulfide bridges present in particular in cases in which $X_1$=S. Preferably, in particular when $X_1$=NH or O, the labile group SE is susceptible to a chemical compound (a target reagent) or an enzyme. An enzyme is defined as a natural protein that catalyzes a chemical reaction.

Preferably, the labile group SE ensures recognition of a target (chemical or enzymatic compound, physicochemical parameter of a medium), and in particular of an enzyme, selectively localized in a tissue or in a target cell type.

SE groups have the feature of being capable of being cleaved from the remainder of the molecule under the action of a stimulus that may in particular be the presence of an enzyme, a chemical compound, or a physicochemical characteristic of the medium in which the probe is located. When SE is an enzymatic substrate, the enzyme then acts as a catalyst for the cleavage between SE and the atom $X_1$ to which it is bonded. A cut of this type is the consequence of hydrolysis in aqueous medium, in which the enzyme acts as a catalyst. Although, the cut here likewise involves hydrolysis, the term "cleavage" is used for the action of an enzyme that is catalytically active for the hydrolysis reaction.

The choice of $X_1$ should be adjusted as a function of the SE group, and in particular of the selected enzyme substrate, in a manner such as to obtain the desired cleavage. In particular, $X_1$ should be an oxygen when SE is an esterase, glycosidase, phosphatase, sulfatase, or glucuronidase substrate, $X_1$ should be NH when SE is a protease substrate, in particular amidase, or transferase, and $X_1$ should be a sulfur when $X_1$-SE is a disulfide bond that is cleaved by a reducing agent.

In particular, depending on the application envisaged for the probes in accordance with the invention, the person skilled in the art could select a substrate for at least one enzyme selected from esterases such as carboxylesterases or lipases; alkaline phosphatases; glucuronidases such as β-glucuronidase; glycosidases; proteases such as metalloproteases; peptidases and amidases.

The SE group is preferably selected in a manner such as to be specific for an enzyme of interest. In contrast, certain enzymes have the capacity for cleaving a different set of SE groups; of these, hexosaminidase and esterases may be mentioned.

Enzymes of this type should be selected in particular from glycosyl groups bonded via their anomeric carbon to the remainder of the molecule, fatty acids bonded via their acyl function to the remainder of the molecule, peptidyl groups bonded to the remainder of the molecule via an acyl function carried by their terminal carbon or by a side chain, or a sulfonyl group forming a sulfonamide with $X_1$ that then represents NH.

In particular, SE may be a glycosidase substrate, and in particular galactosidase, and correspond to a glycosyl group bonded to the remainder of the molecule via its anomeric carbon.

The term "glycosidase" means a glycoside hydrolase enzyme that has the capacity to catalyze the hydrolysis of glycoside bonds in a manner such as to liberate at least one osidic compound.

The term "glycosyl" group means any sugar, monosaccharide or polysaccharide, bonded to the remainder of the molecule via a glycosyl bond, i.e. via its anomeric carbon. The anomeric carbon may adopt the alpha or beta configuration. Examples of the SE groups that may be mentioned are mono-glycosyl groups, i.e., formed by a single saccharide unit and polyglycosyl groups, i.e. formed by several identical or different saccharide units. The saccharide units may in particular be of the hexose or pentose type and selected from galactose, glucose, mannose, gulose, allose, altrose, idose, talose, fucose, fructose, arabinose, lyxose, ribose, and xylose, for example. The saccharide units may have L or D sterochemistry. All of the possible glycosyl groups constituting glycosidase substrates may be used as the SE. The glycosyl units may optionally be functionalized, in particular with an acetyl or amino group. N-acetylhexosamines are examples of the glycosyl group. Usually, the SE group comprises 1 to 50 saccharide units. With a polyglycosyl, it may be a homopolymer or a copolymer with a random, alternating, or block structure.

Examples of SE groups of this type that behave as glycosidase substrates are given below: monoglycosylated groups selected from galactosyl, glucosyl, mannosyl, gulosyl, allosyl, altrosyl, idosyl, talosyl, fucosyl, fructosyl, arabinosyl, lyxosyl, ribosyl, xylosyl, glucuronyl and N-acetylhexosaminyl, and polyglycosylated groups constituted by a plurality (in particular 2 to 20, preferably 3 to 10, and more particularly 4 to 6) of these identical or different monoglycosylated groups.

Examples of glycosidase enzymes that may be targeted by the probes in accordance with the invention that may be mentioned are N-acetyl-β-galactosaminidase; N-acetyl-β-glucosaminidase; α-amylase; α-arabinofuranosidase; α-arabinosidase; β-cellobiosidase; β-chitobiosidase; α-galactosidase; β-galactosidase; α-glucosidase; β-glucosidase; β-glucuronidase; α-maltosidase; α-mannosidase; β-mannosidase; β-xylosidase; β-D-fucosidase; α-L-fucosidase; β-L-fucosidase; L-iduronidase; or cellulase (Orenga, S., James, A. L., Manafi, M., Perry, J. D., & Pincus, D. H. (2009). Enzymatic substrates in microbiology. *Journal of Microbiological Methods*, 75(2), 139-155).

SE may also be a substrate of a galactosidase, and in particular of β-galactosidase, induronidase, glucosidase, N-acetyl-D-glucosaminidase, N-acetyl-D-galactosaminidase, mannosidase, fucosidase, or glucuronidase, more particularly β-glucuronidase.

Examples of SE groups of this type that behave as galactosidase substrates are given below: monoglycosylated groups selected from D-glucuronyl, L-iduronyl, D-glucopyranosyl, D-galactopyranosyl, N-acetyl-D-glucosaminyl, N-acetyl-D-galactosaminyl, D-mannopyranosyl, L-fucopyranosyl, and polyglycosylated groups constituted by a plurality (in particular 2 to 20, preferably 3 to 10, and more particularly 4 to 6) of these monoglycosylated groups, which may be identical or different.

SE may also be an esterase substrate, in particular lipase. Under such circumstances, SE is an acyl group, bonded via its C(O) function to the remainder of the molecule. In particular, SE may be —C(O)Ri in which Ri represents, for example, an alkyl group preferably containing 1 to 20 carbon atoms, an alkenyl group preferably containing 1 to 20 carbon atoms, or a benzyl, aryl, or heteroaryl group.

SE may also be a substrate of a protease or a peptidase, in particular a substrate of cathepsin or metalloprotease, in particular Prostate Specific Membrane Antigen (PSMA).

Under such circumstances, SE is a peptidyl or amino acid group bonded to the remainder of the molecule via an acyl function carried by its terminal carbon or by a side chain.

The term "peptidyl" group means a concatenation of at least two amino acids bonded together via a peptide linkage. In the context of the invention, the amino acid or amino acids present in SE may be natural amino acids or otherwise, but should preferably be selected from the 20 natural amino acids (=proteinogenic), optionally in the form of a salt or in a protected form. The N-terminal function of the terminal amino acid may optionally be in the form of a salt or in a functionalized form. Examples of the salt form that may be mentioned are the hydrochloride, tosylate, or trifluoroacetate form.

Any possible peptidyl or amino acid groups constituting peptidase substrates may be used as the SE group. The amino acids may optionally be functionalized, in particular on the N-terminal end of SE. In particular embodiments, the peptidyl residue SE has at most 10 amino acids, which may be identical or different. The amino acids of the peptidyl residue SE are preferably selected from natural amino acids. However, the N-terminal end of the amino acid or of the peptidyl group may be functionalized with an acyl group, —$COR_0$, $R_0$ being a ($C_1$-$C_6$)alkyl group or a —O—($C_1$-$C_6$) alkyl group. The possible functionalization of the N-terminal end of a given probe with an acyl group, ($R_0CO$—), derives from the fact that certain endoproteases do not interact with a substrate having a free amino group at its end. In addition, this N-terminal functionalization is preferred when SE represents a peptidyl group, while when SE represents an amino acid, its N-terminal function may be free, or preferably is in the form of a salt, as an ammonium compound. Solid phase peptide synthesis (SPPS) using carbamate protective groups (which also constitute "acyl" groups in this context) can often be used for simpler synthesis of a probe having a carbamate at this N-terminal end. With amino-peptidases, it is preferable to use an SE group that represents an amino acid, while with endopeptidases, it is preferable to use an SE group that represents a peptidyl group.

The following peptidyl groups may be mentioned by way of example: Leu (for leucine aminopeptidase), Ser-Gln-Asn-Tyr (the N-terminal portion of the preferred cleavage sequence of the peptidase of HIV-1), Asp-Glu-Val-Asp- (for caspase 3), His-Ser-Ser-Lys-Leu-Gln (for prostate-specific antigen, "PSA"), in which the N-terminal end may be free or be substituted with an acyl group, —$COR_0$, $R_0$ being a ($C_1$-$C_6$)alkyl group or a —O—($C_1$-$C_6$)alkyl group (for example a —COMe group).

The peptidyl or amino acid group is selected for its compatibility with the known sequence selectivity of the targeted peptidase that recognizes it. The peptidyl or amino acid group may be selected for the preferred action that a peptidase involved in certain diseases has on it, as shown in particular in Table 1.

TABLE 1

Examples of peptidases that may act as biomarkers for biological phenomena or for diseases during imagery

| Peptidase | Class | Function | Disease |
| --- | --- | --- | --- |
| Leucine amino-peptidase | Zinc | Post-proteasomal maturation of presented class I peptides | — |
| Caspase-3 | Cys | Apoptosis | Cancer |
| HIV-1 peptidase | Asp | Replication of HIV | AIDS |
| Renin | Asp | Production of angiotensin I | Hypertension |
| Thrombin | Ser | Blood coagulation | Myocardial infarctus |
| Tryptase | Ser | Phagocytosis | Asthma |
| Cathepsin K | Cys | Bone resorption | Osteoporosis |
| ACE | Zinc | Production of angiotensin II | Hypertension |
| Plasmepsins I and II | Asp | Degradation of hemoglobin | Malaria |
| β-Secretase | Asp | Synthesis of amyloid β | Alzheimer's disease |
| PSA (kallikrein III) | Ser | Liquefaction of sperm ejaculate | Prostate cancer |

SE may also be an amidase substrate, which catalyzes the hydrolysis of non-peptide amide bonds, in particular a substrate of penicillin amidases, fatty acid amide hydrolase, or malonamidases.

SE may also be a transferase substrate, which catalyzes the transfer of a functional group from one substrate to another, in particular a transaminase substrate, or glutathione transferase substrate or gamma-glutamyl/transferase substrate. Under such circumstances, SE corresponds to a peptidyl or amino acid group bonded via an acyl function carried by its terminal carbon or by a side chain or a sulfonyl group forming a sulfonamide, in which $X_1$ then represents NH.

Protease substrates are well known and have in particular been described in the "*Handbook of proteolytic enzymes*" (Ralings and Salvesen, 2013, 3$^{rd}$ edition, Elsevier Ltd) and in the online MEROPS database (http://merops.sanger.ac.uk/index.shtml, Bateman et al. Nucleic acid res. 2014, 42, D503), to which reference should be made for further details.

SE may also be a substrate reacting with a chemical compound, and in particular a group forming a disulfide bridge with $X_1$, which is a sulfur atom that is reduced/cleaved by a reducing agent, in particular by dithiothreitol or by the cysteine present in the sample to be analyzed, or a substrate reacting by cleavage of a labile bond in an acidic medium during acidification of the sample being analyzed, and in particular a group forming an acetal bond with $X_1$ that is an oxygen atom, such as the SE groups corresponding to methyloxymethyl (—$CH_2$—O—$CH_3$), methyloxyethyl (—$CH_2$—O—$CH_2CH_3$), methyloxyphenyl (—$CH_2$—O—PH), methyloxyallyl (—$CH_2$—O-allyl).

Definition of Groups A

A is an aromatic group that, after cleavage of the $CX_2$—O bond, permits the formation of a chromophore or fluorophore. This chromophore or fluorophore may correspond directly to the liberated compound A-OH or to its A-O$^-$ form that is formed in aqueous solution, or to a compound resulting from a post-cleavage reaction of the liberated compound A-OH or A-O$^-$ such as a dimerization or to a compound resulting from a post cleavage rearrangement of the compound A-OH or A-O$^-$, for example to result in a tautomeric form. A compound of this type is denoted A'=O.

The term "aromatic group" means a group comprising one or more aromatic rings that may optionally be substituted, said rings possibly comprising one or more heteroatoms selected from nitrogen, oxygen or sulfur atoms and/or one or more carbon atoms in the form of a carbonyl, C=O. A comprises, for example and preferably, 4 to 40 carbon atoms and 0 to 10 heteroatoms selected from nitrogen, oxygen or sulfur atoms. In particular, an aromatic group A may be a monocyclic carbocycle, a bicyclic carbocycle or a polycyclic carbocycle with more than two rings, and preferably containing 5 to 40 links, preferably 6 to 15 links, and comprising at least one aromatic ring, said carbocycle optionally comprising at least one heteroatom selected from oxygen, nitrogen or sulfur atoms integrated into the carbocycle and/or one or more carbon atoms forming the carbocycle in the form of a carbonyl C=O, a carbocycle of this type possibly being unsubstituted or carrying one or more substituents. The aromatic groups in particular comprise aryl and heteroaryl groups, which may be substituted or unsubstituted. Examples of carbocycles of this type in their unsubstituted form that may be mentioned are phenyl, naphthyl, 2-, 3- or 4-pyridinyl, 2- or 3-furoyl, 2- or 3-thiophenyl, pyrrolyl, imidazolyl, pyrazolyl, thiazolyl, oxazolyl, isoxazolyl, pyridinyl, pyrazinyl, pyrimidinyl, tetrazolyl, thiadiazolyl, oxadiazolyl, triazolyl, pyridazinyl, indolyl, and pyronyl.

A chromophore is a molecule that is capable of absorbing a portion of the spectrum of visible light. Examples of a chromophore that may be mentioned are para-nitrophenol and its derivatives, indigoid type dyes obtained after dimerization of the corresponding enol derivative (and thus corresponding to A'=O) that form a precipitate in an aqueous aerobic medium, or indeed compounds such as cyclohexenoesculetin (CHE), alizarin, or hydroxyflavone that form a colored precipitate in the presence of certain metals:

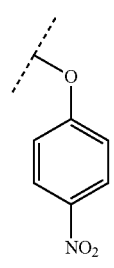

paranitrophenol

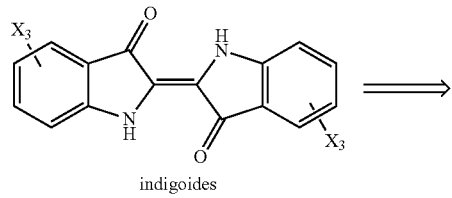

indigoides

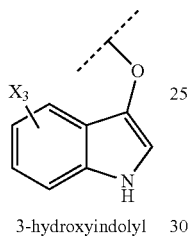

3-hydroxyindolyl

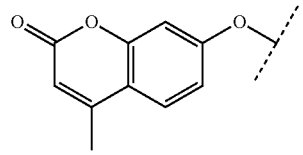

umbelliferone

Alizarin

CHE hydroxyflavone

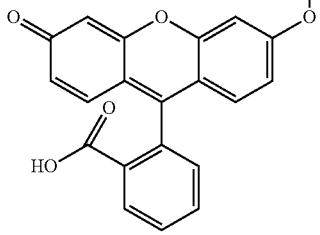

fluorescein

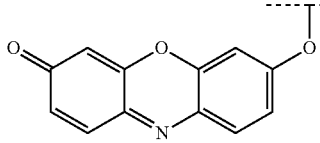

resorufin

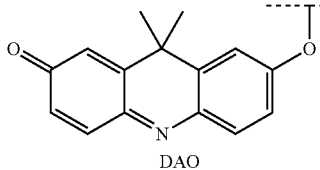

DAO

The hydroxyindolyls may be substituted with one or more $X_3$, which may be identical or different, selected from chlorine, bromine, iodine, or fluorine atoms and positioned on any position of the benzene ring.

A fluorophore is a molecule that is capable of generating fluorescence when it is subjected to excitation with light of a suitable wavelength. "Fluorescence" is the property by means of which a molecule that is excited with light of a given wavelength emits light at a longer wavelength. Fluorescence is a phenomenon that results from the interaction of a fluorophore with an incident photon. This process is known as excitation. Absorption of the photon causes an electron in the fluorophore to move from its basic state into a higher energy level. Next, the electron returns to its original level by emitting a photon. This process is known as fluorescence emission. The fluorophore then emits light at a longer wavelength than that of the absorbed photon. This is simply due to the fact that the energy of the emitted photon is lower than that of the absorbed photon due to the dissipation of energy during the lifetime of the excited state. This definition is given in patent application WO 2004/058787.

Examples of —OA groups that can liberate fluorophores of this type are given below:

Examples of the —OA group permitting the liberation of a fluorophore after rearrangement of the liberated molecule A-OH or A-O⁻ that can be mentioned are the following fluorophores (the second has been described by: Shabat et al. *J. Am. Chem. Soc.* 2012, 134, 20412):

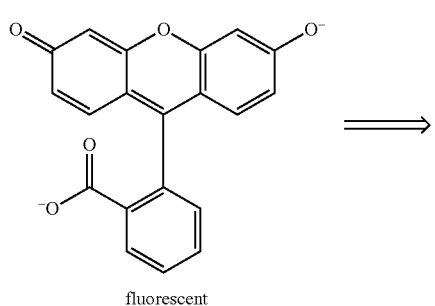

fluorescent

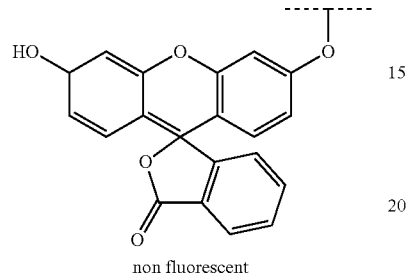

non fluorescent

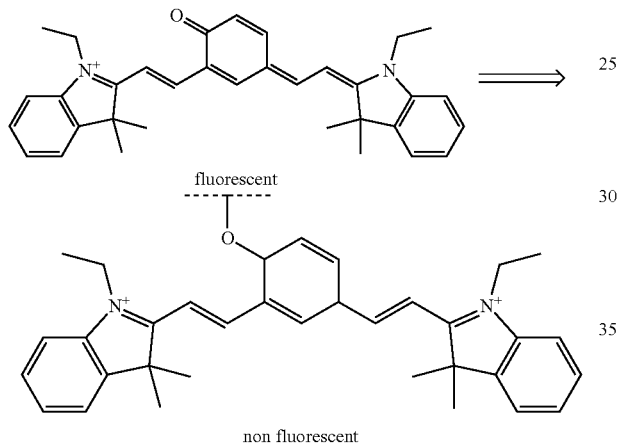

fluorescent non fluorescent

In accordance with particular embodiments, the —OA group is selected in a manner such as to obtain, after cleavage of the C—O bond between the carbon atoms carrying the atom ($X_2$) and the oxygen atom carrying the group A in the compounds with formula (I), a compound AOH that corresponds to an ESIPT fluorophore, which may optionally precipitate out in aqueous solution. An ESIPT fluorophore is a compound that comprises at least one hydroxyl group that is involved in the intramolecular transfer of a proton, allowing the tautomerization of the fluorophore molecule and the emission of fluorescence. Examples of —OA groups of this type have the formula (AA):

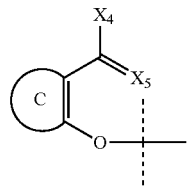

(AA)

in which:
either $X_5$ is an oxygen atom and $X_4$ is a —NH$_2$, —OH, —SH, alkyl, aryl, —O-alkyl, —O-phenyl, —NH-alkyl, —NH-phenyl, —S-alkyl, or —S-aryl group, said alkyl and phenyl groups possibly being substituted or unsubstituted; or $X_5$ represents a nitrogen atom and is bonded to $X_4$, which then represents CH, O, S, N or NH in order to form a substituted or unsubstituted heteroaryl, said substituted or unsubstituted heteroaryl preferably being selected from quinazole, imidazole, benzoimidazole, thiazole, benzothiazole, oxazole, benzooxazole, pyridine, and quinoline; and

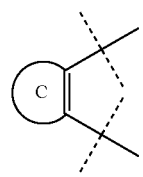

represents an aryl or a heteroaryl, which may be substituted or unsubstituted, for example selected from the phenyl and naphthyl groups, and:

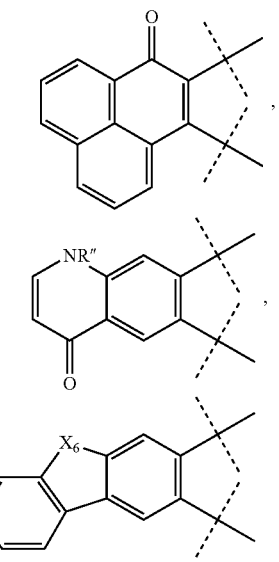

said groups possibly being substituted or unsubstituted;
in which $X_6$ represents S, O, or NR″, and R″ represents a hydrogen atom or a (C$_1$-C$_4$)alkyl group.

When a group —OA, which in the form AOH represents an ESIPT fluorophore, comprises several hydroxyl groups, then the oxygen atom of the —OA group is the oxygen atom of the hydroxyl group that is involved in the transfer of the intramolecular proton. Incorporating this hydroxyl group into the carbamate group of the compounds with formula (I) prevents the formation of the internal hydrogen bond and tautomerization of the fluorophore.

ESIPT fluorophores exhibit a Stokes shift that exceeds 100 nanometers (nm) and frequently reaches 200 nm. All ESIPT fluorophores lose this fluorescence emission, corresponding to a Stokes shift of more than 100 nm, if their phenolic type OH group is alkylated, acylated or functionalized in another manner, which prevents the transfer of a hydrogen atom to the heteroatom $X_5$ in the illustration given with formula (AA), during excitation by irradiation, and thus prevents the fluorescence emission characteristic of the proton transfer process.

Under such circumstances, the group A usually corresponds to a phenyl group that is unsubstituted or substituted and/or that is fused with one or more unsaturated carbocycles optionally comprising a heteroatom such as nitrogen. This group in its phenoxy form, —OA, when it is not bonded to the substrate, corresponds in its protonated form to a phenolic compound HO-A which belongs to the class of ESIPT fluorophores.

—OA groups of the phenoxy type correspond, for example, to the following preferred structures (BB) or (CC):

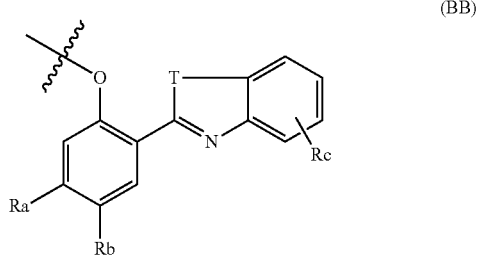

in which
T is —NH—C(O)—, —S—, —O—, —NH, N-alkyl, or N-aryl;
Ra is hydrogen or an electron-attracting carbon-containing substituent such as —CN or —COORd, with Rd representing a ($C_1$-$C_4$)alkyl group, or indeed Ra is —CONReRf, with Re and Rf, which may be identical or different, representing hydrogen or a ($C_1$-$C_4$)alkyl group, or indeed Ra is —CF$_3$ or a 2-oxazolyl, 2-thiazolyl, 2-imidazolyl, 2-benzoimidazolyl, 4-pyrimidinon-2-yl, or quinazolinon-2-yl group;
Rb is hydrogen, a chlorine, bromine, iodine or fluorine atom, —OH, —NH$_2$, —NRgRh, —NHRg, or —ORg, with Rg and Rh each independently representing a ($C_1$-$C_4$)alkyl;
or indeed Ra and Rb are bonded together to form a hydrocarbon chain comprising 4 or 5 links, which may be saturated or unsaturated, substituted or unsubstituted, optionally interrupted by one or more heteroatoms selected from N, S, and O;
Rc is hydrogen, Br, Cl, I, or F;

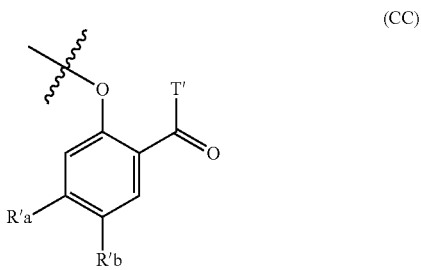

in which:
T' is NH$_2$, OH, an aryl group, a ($C_1$-$C_4$)alkyl group, SH, NHR'c, OR'c, NR'cR'd, or SR'c, with R'c and R'd, which may be identical or different, representing a ($C_1$-$C_4$)alkyl or aryl group;
R'a is hydrogen or an electron-attracting carbon-containing substituent such as —CN, or —COOR'e, in which R'e represents a ($C_1$-$C_4$)alkyl group, or R'a is —CONR'fR'g, in which R'f and R'g, which may be identical or different, represent hydrogen or a ($C_1$-$C_4$)alkyl group, or indeed R'a is —CF$_3$ or a 2-oxazolyl, 2-thiazolyl, 2-imidazolyl, 2-benzoimidazolyl, 4-pyrimidinon-2-yl, or quinazolinon-2-yl;
R'b is hydrogen, a chlorine, bromine, iodine or fluorine atom, —OH, —NH$_2$, —NR'hR'I, or —OR'h, in which R'h and R'i, which may be identical or different, represent a ($C_1$-$C_4$)alkyl group;
or indeed R'a and R'b are bonded together to form a hydrocarbon chain comprising 4 or 5 links, which may be saturated or unsaturated, substituted or unsubstituted, optionally interrupted by one or more heteroatoms selected from N, S, and O.

For more details, reference may in particular be made to applications WO 2013/045854 and WO 2014/020285A, which provide examples of ESIPT fluorophores of this type.

More particular examples of OA groups corresponding to an ESIPT type fluorophore that may be mentioned are as follows:

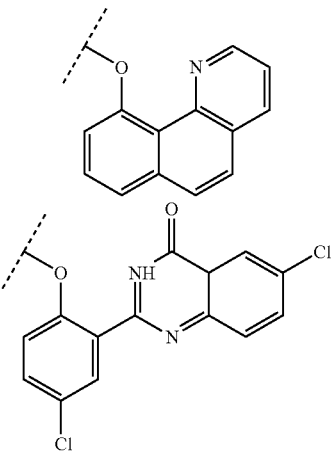

The very large Stokes shift of fluorophores of this type (approximately 170 nm for HPQ (hydroxyphenylquinazolinone) shown on the right hand side or of any analog of HPQ contributes to the excellent sensitivity of the probe and makes the liberated fluorophore readily distinguishable from the native fluorescence that may originate from the biological sample on which the analysis is to be carried out.

Definition of Groups R

R may represent a hydrogen atom or -(L)n-GP, with n equal to 0 or 1.

Very frequently, for synthesis reasons, n=1 and L is a linker arm, and in particular a -(L1)m1-(L2)m2-(L'1)m'1- arm (in the direction piperazine->group GP), in which:
L1 and L'1, which may be identical or different, are selected from —O—, —NH—, —N($C_{1-6}$)alkyl-, —N(phenyl)-, —N(aryl)-, —C(O)—, —C(O)O—, —OC(O)—, —OC(O)—O—, —NHC(O)—O—, —OC(O)—NH—, —NHC(O)—NH—, —S—, —SO$_2$—, —N=N—, —NHC(O)—, and —CONH—;
L2 is selected from the following bivalent groups: ($C_{1-20}$)alkyl, ($C_{1-20}$)alkenyl, ($C_{1-20}$)alkynyl, ($C_{6-24}$)aryl, ($C_{7-44}$)alkylaryl, ($C_{7-44}$)alkenylaryl, ($C_{7-44}$)alkynylaryl, ($C_{7-44}$)alkylcycloalkyl, ($C_{7-44}$)alkenylcycloalkyl, ($C_{7-44}$)alkynylcycloalkyl, ($C_{7-44}$)alkylheterocycloalkyl, ($C_{7-44}$)alkenylheterocycloalkyl, ($C_{7-44}$)alkynylheterocycloalkyl; said groups possibly being interrupted by or terminating in a triazole group and possibly being unsubstituted or substituted, in particular with one or more substituents selected from $(C_{1-10})$alkoxy, $(C_{1-10})$alkyl, $(C_{6-10})$aryl, amido, imido, phosphido, nitrido, $(C_{1-10})$alkenyl, $(C_{1-10})$alkynyl, and —OH; and m1, m'1 and m2, which may be identical or different, are equal to 0 or 1.

The arm L, when it is present, is selected in order to distance the GP group from the piperazine or for synthesis reasons. In accordance with a preferred embodiment, L represents -(L1)m1-(L2)m2-(L'1)m'1 in which L1=—C(O)—, m1=m2=1, m'1=1 or 0 and L2 and L'1 are as defined above, and in particular L represents —C(O)—(CH$_2$)p-L3- in which p is equal to 1, 2, 3, or 4 and L3 is a triazole group and in particular a 1H-1,2,3-triazole group.

GP is a hydrosolubilizing group.

The term "hydrosolubilizing group", means a hydrophilic group that can be used to improve the solubility of the probe, in particular relative to a probe that only differs by replacement of the nitrogen atom carrying the L-GP by a CH$_2$, in order to obtain a piperidine as described in the applications WO 2013/045854 and WO 2014/020285. Examples of hydrosolubilizing groups that may be mentioned are groups that are capable of forming a charged species in aqueous solution. Examples of the hydrosolubilizing group GP that may be mentioned are functions $F_1$ selected from amines (primary, secondary, or tertiary), amidine, guanidine or tetrazole; functions $F_2$ selected from anionic functions of the carboxylate, sulfonate, or phosphate type; groups comprising one or more of these functions $F_1$ and/or $F_2$; polyethylene glycols; sugars or polysaccharides such as glucose, galactose, and mannose; peptide groups such as polylysine, polyarginine, TAT peptides, etc. Examples of amine functions that may be mentioned are —NH$_2$, —NH(C$_{1-4}$)alkyl, and dialkylamines in which the alkyl groups are identical or different and contain 1 to 4 carbon atoms. The term "groups comprising one or more of these functions $F_1$ and/or $F_2$" means an alkyl group (such as the (C$_{3-6}$)alkyls), an aryl group (such as an aryl group containing 6 carbon atoms), a heteroaryl group (such as a heteroaryl group containing 6 carbon atoms) in which one or more hydrogen atoms of these groups has(have) been substituted with one or more functions $F_1$, or with one or more functions $F_2$, or indeed at least one hydrogen atom has been substituted with a function $F_1$ and another hydrogen atom has been substituted with a function $F_2$.

Definition of the Terms Used in the Definition of the Probes

The term "acyl function" means a function:

The term "alkyl" group, unless otherwise specified, means a saturated, linear or branched hydrocarbon chain. Alkyl groups containing 1 to 6 carbon atoms are preferred. Particular examples of alkyl groups containing 1 to 6 carbon atoms that may be mentioned, denoted C$_{1-6}$ alkyl or (C$_1$-C$_6$)alkyl, are methyl, ethyl, n-propyl, iso-propyl, n-butyl, tert-butyl, sec-butyl, n-pentyl, and n-hexyl groups.

The term "aryl" group means a mono-, bi-, or poly-cyclic carbocycle comprising at least one aromatic group, for example a phenyl, cinnamyl, or naphthyl group. Aryl groups containing 6 to 12 carbon atoms are preferred. Phenyl is the particularly preferred aryl group.

When a "substituted" group is indicated, this means that it is substituted with one or more substituents, in particular selected from chlorine, bromine, iodine, or fluorine atoms, cyano, alkyl, fluoroalkyl, trifluoromethyl, alkenyl, alkynyl, cycloalkyl, aryl, heterocycloalkyl, amino, alkylamino, dialkylamino, hydroxy, alkoxy, aryloxy, —COOH, and nitro groups, acyl groups, aromatic groups (in particular aryl and heteroaryl); said alkenyl, alkynyl, cycloalkyl and heterocycloalkyl groups, acyl groups, and aromatic groups may themselves be unsubstituted or substituted. The terms used for the definition of these substituents are those usually recognized by the person skilled in the art.

As is conventional, the term "alkenyl" designates a hydrocarbon chain, which may be linear or branched, containing at least one double bond, and preferably containing 2 to 20 carbon atoms, and preferably 2 to 6 carbon atoms; the term "alkynyl" denotes a linear or branched hydrocarbon chain containing at least one triple bond and preferably containing 2 to 12 carbon atoms, more preferably 2 to 6 carbon atoms; the term "fluoroalkyl" denotes a hydrocarbon chain, which may be saturated, linear or branched, in which at least one hydrogen atom has been replaced by a fluorine atom, and preferably containing 2 to 12 carbon atoms, preferably 2 to 6 carbon atoms; the terms "alkoxy" and "aryloxy" respectively denote an O-alkyl, and an O-aryl.

The term "cycloalkyl" means a saturated hydrocarbon group constituted by at least one cycle, which may be bridged. Alkyl groups containing 3 to 12 carbon atoms are preferred. Examples that may be mentioned are the cyclopropyl, cyclobutyl, cyclopentyl, cyclohexyl, cycloheptyl, and adamantyl groups.

The term "heterocycloalkyl" means a cycloalkyl group as defined above, in which at least one carbon atom has been replaced by a heteroatom selected from O, S, or N. Examples of heterocycloalkyls that may be mentioned are the piperidinyl, piperazinyl, morpholinyl, tetrahydropyranyl etc. groups.

The term "heteroaryl" group means a mono-, bi-, or polycyclic carbocycle preferably containing 6 to 12 links, and containing at least one aromatic group and at least one heteroatom selected from oxygen, nitrogen, or sulfur atoms integrated into the carbocycle. Examples of heteroaryl groups that may be mentioned are 2-, 3- or 4-pyridinyl, 2- or 3-furoyl, 2- or 3-thiophenyl, pyrrolyl, imidazolyl, pyrazolyl, thiazolyl, oxazolyl, isoxazolyl, pyridinyl, pyrazinyl, pyrimidinyl, tetrazolyl, thiadiazolyl, oxadiazolyl, triazolyl, pyridazinyl, and indolyl. Heteroaryls also contain groups of the type in which one or more carbon atom(s) of the carbon cycle is(are) in the form of a carbonyl function, C=O.

The term "acyl group" means a group bonded via the carbon of an acyl function, C=O, and in particular a —CONH$_2$, —COOH, —COaryl, —CO(C$_{1-4}$)alkyl, —COSH, —CONHR"$_a$, —CONR"$_a$R"$_b$, or —COSR"$_a$ group, in which R"$_a$ and R"$_b$, which may be identical or different, represent a (C$_1$-C$_4$) alkyl or aryl group.

The term "(C$_{7-44}$)alkylaryl", "(C$_{7-44}$)alkenylaryl", "(C$_{7-44}$)alkynylaryl" respectively mean an alkyl, alkenyl or alkynyl chain commencing, being interrupted by, or terminating in an aryl group. Alkylaryl, alkenylaryl, and alkynylaryl groups containing 7 to 22 and preferably 7 to 16 carbon atoms are preferred.

Preparation of Probes in Accordance with the Invention

The compounds used in the context of the invention are prepared in accordance with conventional techniques. They may in particular be obtained using methods analogous to those used in the examples.

The compounds in accordance with the invention may be obtained in accordance with Scheme 2 below, in which A, X$_1$, X$_2$, and SE are as defined for probes with formula (I) and $P_1$ and $P_2$ are temporary protective groups for the amine functions, in particular under the reaction conditions employed, Y is a leaving group of the Cl, para-nitrophenol, imidazole or N-methylimidazolium or N-hydroxysuccinimide type, and Rp represents R or a temporary protective group for the amine functions, in particular under the reaction conditions employed, or Rp is a precursor group for the group R.

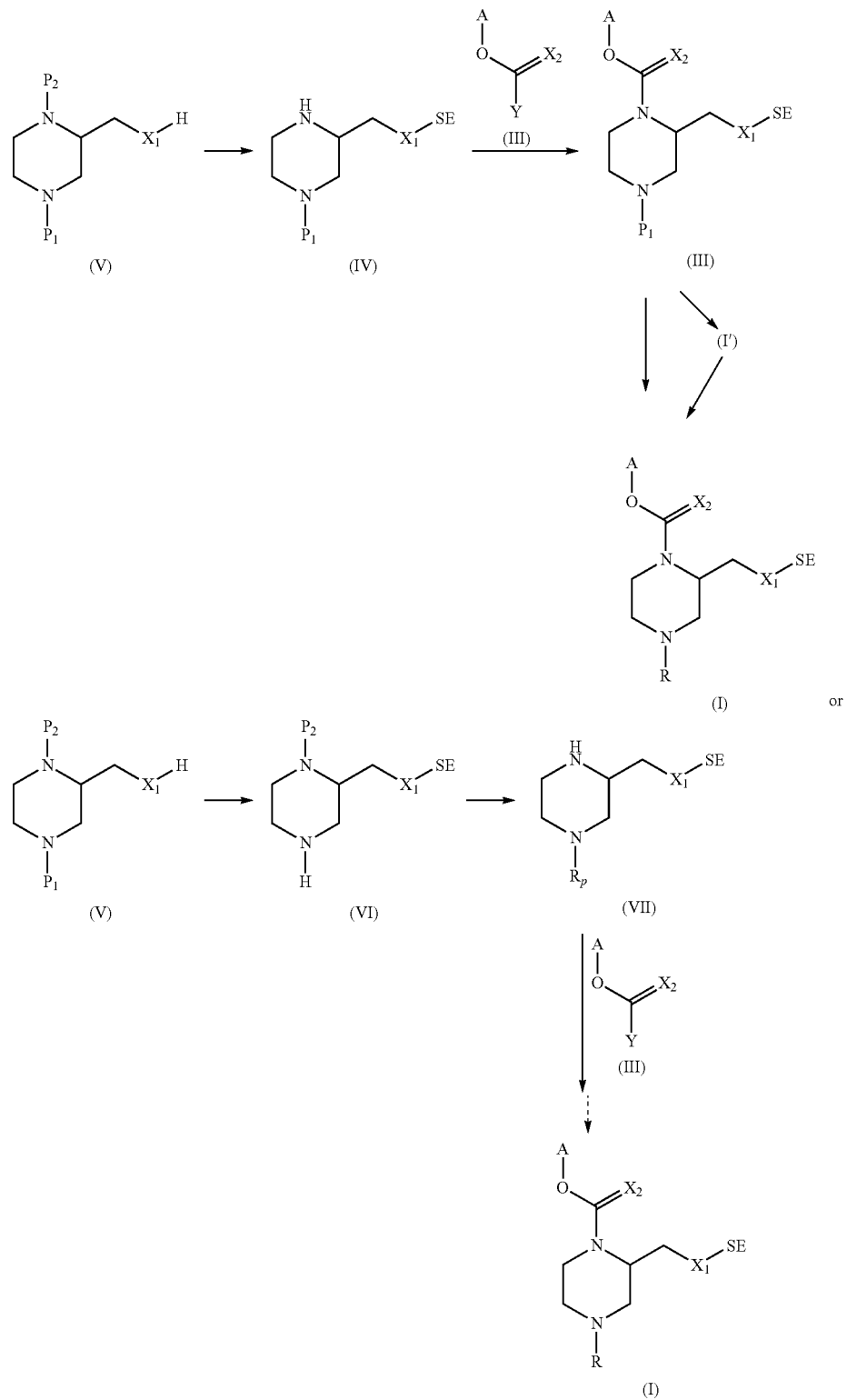

The term "protective group for the amines" means protective groups such as those described in Protective Groups in Organic Synthesis, Greene T. W. and Wuts P. G. M., ed John Wiley and Sons, 2006 and in Protecting Groups, Kocienski P. J., 1994, Georg Thieme Verlag. Examples of groups of this type that may be mentioned are benzyl groups (Bn), —C(O)OR'$_1$ groups in which R'$_1$ represents an alkyl or alkenyl group containing 1 to 12 carbon atoms, or a —(CH$_2$)$_{m3}$R"$_1$ group in which R"$_1$ represents an aryl, cycloalkyl or fluorenyl group and m3 is equal to 0, 1, 2, or 3, and in particular carbobenzyloxy (Cbz), ter-butyloxycarbonyl (Boc) and 9-fluorenylmethyloxycarbonyl (Fmoc), allyloxycarbonyl (Alloc) groups.

The compounds (V) may in particular be obtained from commercial piperazine. By following a similar but modified procedure from that described in Org. Lett. 2010, 12, 4176, it is possible to form the compound (V) from doubly protected piperazine, in which one of the groups is a butyloxycarbonyl (Boc) group, by means of an ortholithiation reaction followed by a reaction with paraformaldehyde in order to form the compound (V) where $X_1$=O. The amine derivative (V) where $X_1$=NH may then be obtained, for example by means of a Gabrielle synthesis, while the compound (V) where $X_1$=S may be obtained by nucleophilic substitution.

Preferably, it is also possible to use the methods illustrated in Schemes 3 and 4, which require fewer steps when $X_1$=O or NH in order to prepare compounds with formula (VII). In Schemes 3 and 4, A, $X_1$, $X_2$, and SE are as defined for probes with formula (I) and $R_2$ is an alkyl group containing 1 to 4 carbon atoms, $R_3$ is a temporary protective group for the amine functions, in particular under the reaction conditions employed, and Y is a leaving group of the CI or para-nitrophenol, imidazole or N-methylimidazolium or N-hydroxysuccinimide type, and Rp represents R or a temporary protective group for the amine functions, in particular under the reaction conditions employed, or Rp is a precursor group for the group R.

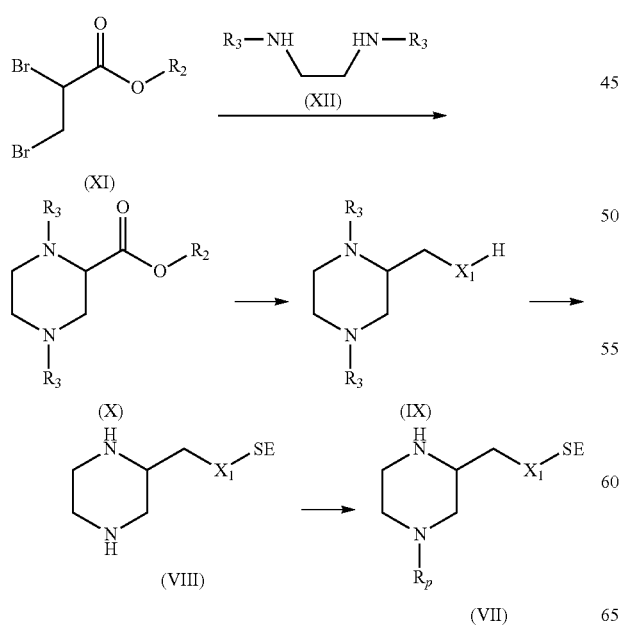

Scheme 3:

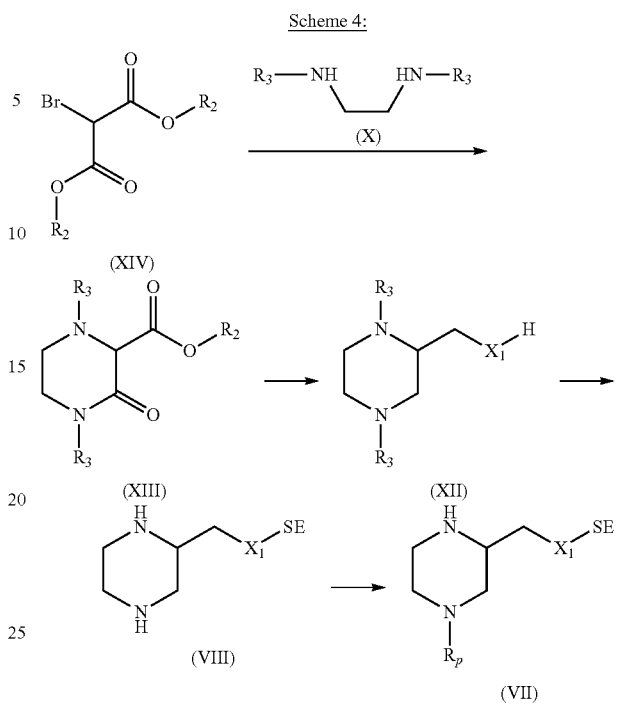

Scheme 4:

In the procedure described in Scheme 3, the piperazine cycle is obtained via a double nucleophilic substitution of a compound of the ethylene diamine (X) type on derivatives of the commercial starting product of the type (XI).

In the procedure described in Scheme 4, the piperazine cycle is obtained by reduction of a piperazinone cycle (XIII), which is in turn synthesized from a bromomalonate (XIV) and from a compound of the ethylene diamine (X) type.

The groups R that are other than H, which correspond to a group L-GP, may be introduced by means of nucleophilic type substitution, reducing amination or amide bond formation type reactions. The bond between the groups L and GP may be obtained using a great number of synthesis pathways, depending on the chemical functions present on the linker arm L. Examples that may be mentioned are ligation reactions such as nucleophilic substitutions, peptide linking, cycloadditions such as the Huisgen or Diels-Alder cycloaddition, or palado-catalyzed couplings such as Sonogashira or Heck coupling.

It is possible in between to form an intermediate compound with formula (I'), in which Rp is a precursor group of a group R or Rp is a temporary protective group for the amines. In particular, intermediates with the following formula form an integral part of the invention:

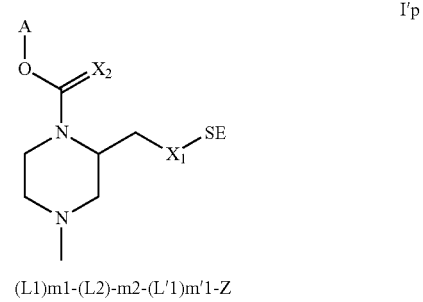

(L1)m1-(L2)-m2-(L'1)m'1-Z

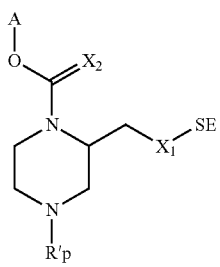
I″p as well as their salts, solvates, or hydrates;
in which:
A, X$_1$, X$_2$, SE, L1, L'1, L2, m1, m'1, and m2 are as defined for (I);
Z represents C≡CH, N3, a N-oxysuccinimide or maleimide function; and
R'p represents a protective group for the amine functions, preferably selected from benzyl groups, —C(O)OR'$_1$ groups in which R'$_1$ represents an alkyl or alkenyl group containing 1 to 12 carbon atoms or a —(CH$_2$)$_{m3}$R"$_1$ group in which R"$_1$ represents an aryl, cycloalkyl or fluorenyl group and m3 is equal to 0, 1, 2, or 3. Examples of preferred groups R'p that may be mentioned are carbobenzyloxy, tert-butyloxycarbonyl, 9-fluorenylmethyloxycarbonyl, and allyloxycarbonyl.

Furthermore, in some cases a compound with formula (I) could act as an intermediate in the preparation of another compound with formula (I). This is the case in particular with compounds with formula (I) in which GP=—COOH or —NH$_2$ that could in particular be used to form compounds in which L'1=—CONH— or —NHCO— and m'1=1.

The starting reagents are commercially available or readily accessible. The molecules with formula (I) are thus relatively easy to access chemically and may be obtained at a preparation cost that is relatively low for the technical field under consideration.

The salts of the compounds in accordance with the invention are prepared in accordance with techniques that are well known to the person skilled in the art. The salts of the compounds with formula (I) in accordance with the present invention include those with acids or bases, depending on the substituents present. These acids or bases may be selected from mineral and organic acids and bases that can be used to result in suitable separation or crystallization of the compounds with formula (I), as well as physiologically acceptable salts, i.e. salts compatible with in vivo and in vitro applications. Suitable acids that may be mentioned include: oxalic acid or an optically active acid, for example a tartaric acid, a dibenzoyltartaric acid, a mandelic acid, or a camphorsulfonic acid, and those that form physiologically acceptable salts, such as hydrochlorides, hydrobromides, sulfates, hydrogenosulfates, dihydrogenophosphates, maleates, fumarates, 2-naphthalenesulfonates, para-toluenesulfonates, mesylates, besylates, or isothionates. Examples of appropriate bases that may be mentioned include: lysine, arginine, meglumine, benethamine, benzathine, and those that form physiologically acceptable salts such as sodium, potassium or calcium salts.

Examples of compounds in the hydrated form that may be mentioned include semi-hydrates, monohydrates, and poly-hydrates.

The term "solvate" means a form of a compound associated with one or more molecules of solvent, in particular used during its synthesis or during its purification, without it in any way being in solution therein.

The various compounds with formula (I) in accordance with the invention may be in any of the possible optical isomeric forms, optionally mixed in any proportions, unless otherwise specified. In accordance with a particular embodiment, the compounds in accordance with the invention comprising an asymmetric carbon are in a racemic form, the R and S forms being in substantially equal proportions. In accordance with another embodiment, the compounds with formula (I) of the invention may be in a form that is enriched in one diastereoisomer or enantiomer, with an excess of diastereoisomer or enantiomer of more than 80%, or even more than 95%, or even in a pure isomeric form, i.e. with an excess of diastereoisomer or enantiomer of more than 99%.

The compounds (I) could be isolated in a form that is enriched in a diastereoisomer or enantiomer using conventional separation techniques: as an example, it would be possible to use fractional re-crystallization of a racemic salt with an optically active acid or a base in accordance with a principle that is well known or, more usually, using conventional chiral or non-chiral phase chromatographic techniques.

In the context of the invention, all of the definitions and preferred embodiments for A, R, X$_1$, X$_2$, and SE could be combined.

In particular, the probes in accordance with the invention have one or the other of the following characteristics, or even all of the following characteristics:
X$_2$=O;
either X$_1$=O and SE is a glycosidase substrate or glucuronidase substrate and corresponds to a glycosyl group bonded to the remainder of the molecule via its anomeric carbon, or SE is an esterase substrate and corresponds to a —C(O)Ri group in which Ri represents, for example, an alkyl group preferably containing 1 to 20 carbon atoms, an alkenyl group preferably containing 1 to 20 carbon atoms, a benzyl, aryl or heteroaryl group, or X$_1$=NH and SE is a protease or peptidase substrate and corresponds to a peptidyl group bonded via an acyl function carried by its terminal carbon or by a side chain;
R represents -L-GP in which:
L preferably represents -(L1)m1-(L2)m2-(L'1)m'1 in which L1=—C(O)—, m1=m2=1, m'1=1 or 0, and L2 and L'1 are as defined above, and in particular L represents —C(O)—(CH$_2$)p-L3- with p equal to 1, 2, 3, or 4 and L3 is a triazole group and in particular a 1H-1,2,3-triazole group; and
GP is preferably a function F$_1$ selected from the functions ammonium, carboxylate, sulfonate and phosphate, and from polyethylene glycols;
A one of the groups that have been specifically described in the present patent application.

The probes in accordance with the invention are attractive for a number of high sensitivity applications in the life sciences, and in particular: (1) high yield screening of an activity, in particular an enzyme activity, expressed by bacterial colonies on a gel plate (colony analysis); (2) the in vitro detection of an activity, in particular of an enzymatic activity in biological liquids (hematology and the like); (3) the detection of an activity, in particular an enzymatic activity, in a single cell by flow cytometry, (4) visualization of an activity, in particular of an enzyme activity, intracellularly in cells under culture (fluorescence microscopy and confocal microscopy); (5) the histochemical detection of an enzyme (on the tissue scale); and also (6), in vivo molecular imagery.

Thus, the probes in accordance with the present invention have a large number of potential applications. Examples of applications of this type include the design of analyses on bacterial colonies. These are currently carried out on a gel plate (Petri dish) where up to 3000 colonies can be distinguished without having to separate them out actively in separate compartments such as wells contained in a multiple well plate. It is possible, for example, to design tests on clinical samples that can be used to identify a pathogenic line of interest from a series of bacterial lines.

The probes in accordance with the invention may also be used in imaging by macroscopic fluorescence, i.e. on the scale of a whole organism. Under such circumstances, the probe penetrates into the cell wall in order to reach the activity of interest (a stimulus such as an enzyme, a chemical compound, or a physicochemical characteristic of a medium in which the probe is located).

The following examples illustrate the invention, but are not in any way limiting in nature.

ABBREVIATIONS EMPLOYED

DCM: dichloromethane TFA: trifluoroacetic acid
Boc: tert-butyloxycarboxyl Me: methyl
Ac: acetyl HOBt: 1-hydroxybenzotriazole
sBu: sec-butyl HATU: 1-[bis(dimethylamino)methylene]-1H-1,2,3-triazolo[4,5-b]pyridinium 3-oxide hexafluorophosphate
Et: ethyl AT: ambient temperature
DIAD: diisopropyl azodicarboxylate AMC: 7-amino-4-methylcoumarin
THF: tetrahydrofuran DCC: Dicyclohexylcarbodiimide
DMF: N,N-dimethylformamide iPr: isopropyl
δ: chemical displacement (ppm) RFU: arbitrary fluorescence unit
UA: arbitrary absorbance unit $\lambda_{ex}$: excitation wavelength (nm)
$\lambda_{em}$: emission wavelength (nm) NMR: nuclear magnetic resonance
LC: liquid chromatography MS: mass spectroscopy
ESI: electrospray ionization $R_f$: retention factor
J: H—H coupling constant (Hz) s: singlet
d: doublet t: triplet
dd: doublet of doublets td: triplet of doublets
m: multiplet br: broad signal
v: volume
Equipment Used for Characterizations The NMR spectra were obtained at 297K using a Bruker AVANCE 300 spectrometer (300 MHz & 75 MHz for $^1$H and $^{13}$C, respectively) or a Bruker AVANCE 500 spectrometer (500 MHz & 125 MHz for $^1$H and $^{13}$C, respectively).

The low resolution mass measurements were obtained using an AGILENT 1100 SL mass spectrometer coupled with liquid chromatography.

The thin layer chromatography analyses (TLC) were carried out on 60 angstrom (Å) silica gel plates deposited on aluminum (Aldrich).

The high resolution mass measurements were obtained using a Bruker MicrOTOFQ II mass spectrometer.

The fluorescence or absorbance measurements were obtained using an EnSpire plate fluorimeter from Perkin-Elmer.

A—SYNTHESE

I—Preparation of Intermediate 8, N-((4-benzylpiperazin-2-yl)methyl)-2-phenylacetamide, in the Form of a Salt with Trifluoroacetic Acid a) Preparation of Compound 2: N-Boc-piperazine

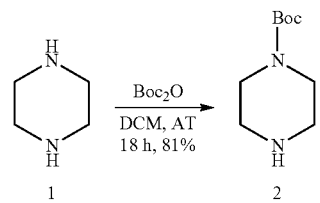 [SMILES: "Boc2O" ; C1CNCCN1 ; CC(C)(C)OC(=O)N1CCNCC1]

A solution of $Boc_2O$ (8.07 grams (g), 50 millimoles (mmol), 1.0 equivalent (eq)) in DCM (150 milliliters (mL)) was added dropwise to a solution of piperazine 1 (10.0 g, 100 mmol, 2.0 eq) in DCM (300 mL) over a period of 3 hours (h) at ambient temperature (AT). At the end of addition, the reaction mixture was stirred at AT for 18 h. The mixture was then concentrated by evaporation, in order to obtain an approximate final volume of 100 mL. This solution was then washed with a saturated aqueous solution of $NaHCO_3$ (2×100 mL) and once with brine (100 mL). The organic phase was dried with $Na_2SO_4$, filtered and evaporated off in order to obtain the compound 2 in the form of a colorless oil that crystallized slowly (7.57 g, 40 mmol, yield: 81%).

$^1$H-NMR (300 megahertz (MHz), $CDCl_3$): δ=3.33 (t, J=5 Hz, 4H), 2.75 (t, J=5 Hz, 4H), 1.67 (s, 1H), 1.41 (s, 9H) parts per million (ppm).

$^{13}$C-NMR (75 MHz, $CDCl_3$): δ=154.9, 79.5, 56.3, 46.0, 44.8, 30.4, 28.5 ppm.

MS: ESI: $[M+H]^+$ m/z found 187.3, calculated 187.3 b) Preparation of Compound 3: N-Boc-N'-benzyl-piperazine

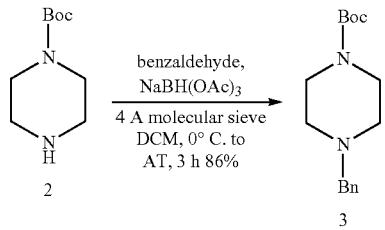 [SMILES: CC(C)(C)OC(=O)N1CCNCC1 ; "benzaldehyde,NaBH(OAc)3" ; CC(C)(C)OC(=O)N1CCN(Cc2ccccc2)CC1]

NaBH(OAc)$_3$ (17.6 g, 80.6 mmol, 1.5 eq) was added in several portions to a solution of compound 2 (10.0 g, 5.7 mmol, 1.0 eq), benzaldehyde (5.5 mL, 53.7 mmol, 1.0 eq) and 4 Å molecular sieve in DCM (200 mL) cooled to 0° C. The reaction medium was stirred at 0° C. for 1 h then at AT for 2 h. At the end of the reaction, the mixture was filtered and the filtrate was washed three times with a saturated aqueous solution of NaHCO$_3$ (3×150 mL). The organic phase was dried with Na$_2$SO$_4$, filtered and evaporated off. The unrefined reaction medium was purified using silica gel column chromatography (eluent: initially pure DCM, then DCM:MeOH/95:5/v:v) in order to obtain the compound 3 in the form of a colorless oil that crystallized slowly (12.8 g, 46 mmol, yield: 86%).

¹H-NMR (300 MHz, CDCl₃): δ=7.29 (m, 5H), 3.52 (s, 2H), 3.45 (t, J=5 Hz, 4H), 2.40 (t, J=5 Hz), 1.48 (s, 9H) ppm.

¹³C NMR (75 MHz, CDCl₃) δ=154.90, 137.98, 129.25, 128.38, 127.26, 79.63, 63.18, 52.98, 43.61, 28.54 ppm.

MS: ESI: [M+H]⁺ m/z found 277.3, calculated 277.3

R$_f$=0.32 (petroleum ether:ethyl acetate/8:2/v:v)

c) Preparation of Compound 4: tert-butyl 4-benzyl-2-(hydroxymethyl)Piperazine-1-carboxylate

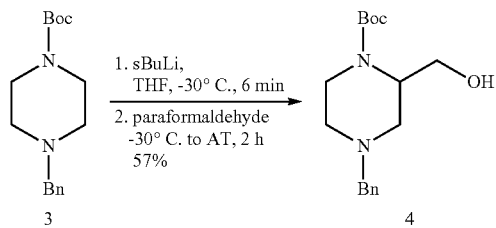 [SMILES: CC(C)(C)OC(=O)N1CCN(Cc2ccccc2)CC1 ; CC(C)(C)OC(=O)N1CCN(Cc2ccccc2)CC1CO]

The compound 3 (1.0 g, 3.6 mmol, 1.0 eq) was dissolved in anhydrous THF (20 mL) in a pre-dried drum and placed under an inert atmosphere of argon. This solution was cooled to −30° C. and sBuLi (1.3 molar (M) in cyclohexane, 4.2 mL, 1.5 eq) was added dropwise. The reaction mixture was stirred at −30° C. for 6 minutes (min) before introducing paraformaldehyde (350 milligrams (mg), 11.6 mmol, 3.2 eq) rapidly, in a single portion. This suspension was stirred at −30° C. for 30 min, and 1 h 30 at AT before being quenched with the aid of a saturated aqueous solution of NH₄Cl (20 mL). The organic phase was separated out and the aqueous phase was washed twice with Et₂O (2×20 mL). The organic phases were combined, dried with Na₂SO₄, filtered and evaporated off. The unrefined reaction medium was purified using silica gel column chromatography (eluent: petroleum ether:ethyl acetate/7:3/v:v) in order to obtain the compound 4 in the form of a yellow oil (625 mg, 2.0 mmol, yield: 57%).

¹H-NMR (500 MHz, CDCl₃): δ=7.32 (m, 5H), 4.12 (br s, 1H), 3.92 (m, 3H), 3.54 (s, 2H), 3.40 (br s, 1H), 3.04 (d, J=11.6 Hz, 1H), 2.86 (d, J=8.7 Hz, 1H), 2.33 (dd, J=11.6 Hz, 3.9 Hz, 1H), 2.13 (td, J=11.6 Hz, 3.9 Hz, 1H), 1.49 (s, 9H) ppm.

¹³C-NMR (125 MHz, CDCl₃): δ=155.3, 137.3, 129.0, 128.6, 127.5, 80.0, 66.5, 63.1, 55.1, 52.6, 51.4, 41.7, 28.5 ppm.

MS: ESI: [M+H]⁺ m/z found 307.2, calculated 307.2

R$_f$=0.28 (petroleum ether:ethyl acetate/7:3/v:v)

d) Preparation of Compound 5: tert-butyl 4-benzyl-2-((1,3-dioxoisoindolin-2-yl)Methyl)Piperazine-1-carboxylate

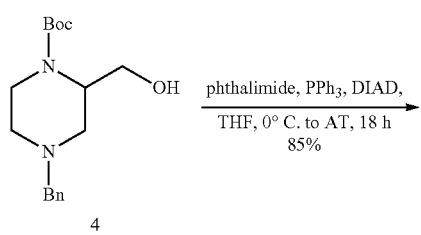

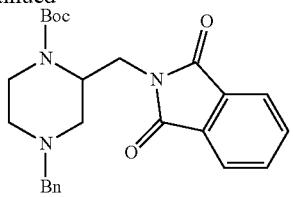

DIAD (845 µL, 4.03 mmol, 1.2 eq) was added dropwise to a solution, cooled to 0° C., of compound 4 (1.03 g, 3.36 mmol, 1.0 eq), triphenylphosphine (1.07 g, 4.03 mmol, 1.2 eq) and phthalimide (600 mg, 4.03 mmol, 1.2 eq) in anhydrous THF (20 mL). The reaction mixture was stirred at 0° C. for 30 min then at AT for 18 h. The volatile compounds were evaporated off and the resulting oil was purified using silica gel column chromatography (eluent: petroleum ether: ethyl acetate/8:2/v:v) in order to obtain the compound 5 in the form of a white solid (1.20 g, 2.76 mmol, yield: 82%).

¹H-NMR (500 MHz, CDCl₃): δ=7.79 (m, 4H), 7.30 (m, 5H), 4.55 (m, 1.5H), 4.45 (m, 0.5H), 3.98 (d, J=13 Hz, 0.6H), 3.75 (d, J=12 Hz, 0.4H), 3.48 (m, 4H), 2.28 (m, 2H), 2.18 (m, 1H), 2.05 (m, 1H), 1.08+1.03 (2×s, 9H) ppm.

¹³C-NMR (125 MHz, CDCl₃): δ=168.5, 168.2, 167.9, 155.1, 154.4, 138.2, 134.5, 134.1, 133.7, 132.8, 132.4, 129.0, 128.7, 128.5, 127.4, 123.7, 123.4, 123.3, 79.7, 62.9, 54.5, 53.3, 50.3, 48.8, 40.1, 38.6, 37.8, 28.4, 27.9 ppm.

MS: ESI: [M+H]⁺ m/z found 436.3, calculated 436.2

R$_f$=0.32 (petroleum ether:ethyl acetate/8:2/v:v)

e) Preparation of Compound 6: tert-butyl 2-(aminomethyl)-4-benzylpiperazine-1-carboxylate

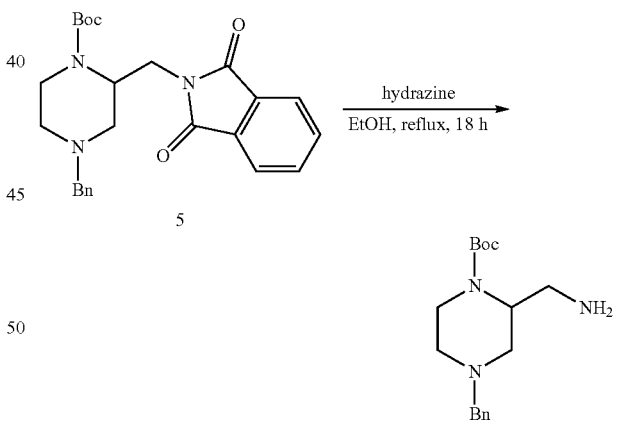

Hydrazine monohydrate (620 mg, 12 mmol, 4.0 eq) was added to a solution of compound 5 (1.20 g, 2.76 mmol, 1.0 eq) in EtOH (30 mL) and the reaction mixture was heated under reflux for 18 h. At the end of the reaction, the suspension was cooled to AT and filtered. The filtrate was evaporated off under reduced pressure to provide a solid that was re-suspended in DCM (50 mL), filtered once again and the filtrate was washed twice with a saturated aqueous solution of NaHCO₃ (2×50 mL) and once with brine (50 mL). The organic phase was dried with Na₂SO₄, filtered and evaporated off in order to obtain the compound 6 (610 mg)

in the form of an oil. This product was used in the next step without any further purification.

¹H-NMR (500 MHz, CDCl₃): δ=7.35 (m, 5H), 3.97 (br s, 2H), 3.57 (d, J=13.2 Hz, 1H), 3.43 (d, J=13.2 Hz, 1H), 3.07 (dd, J=13.1, 7.0 Hz, 1H), 2.94 (dd, J=13.1, 7.0 Hz, 1H), 2.81 (m, 2H), 2.10 (m, 2H), 1.50 (s, 9H) ppm.

¹³C-NMR (125 MHz, CDCl₃): δ=155.33, 138.36, 128.76, 128.49, 128.35, 128.13, 127.19, 79.74, 62.82, 53.55, 53.30, 53.13, 48.55, 41.64, 28.48, 21.99 ppm.

MS: ESI: [M+H]⁺ m/z found 306.3, calculated 306.2 f) Preparation of Compound 7: tert-butyl 4-benzyl-2-((2-phenylacetamido)methyl)piperazine-1-carboxylate

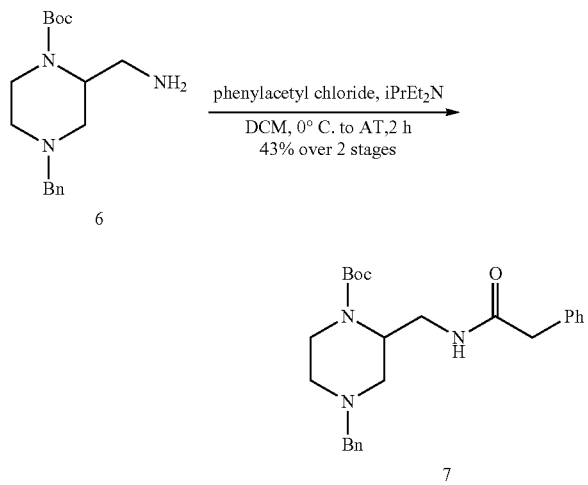 [SMILES: CC(C)(C)OC(=O)N1CCN(Cc2ccccc2)CC1CN ; CC(C)(C)OC(=O)N1CCN(Cc2ccccc2)CC1CNC(=O)Cc1ccccc1]

A solution of phenylacetyl chloride (318 µL, 2.35 mmol, 1.2 eq) in anhydrous DCM (5 mL) was added dropwise to a solution, cooled to 0° C., of compound 6 (600 mg, 1.96 mmol, 1.0 eq) and diisopropylethylamine (DIPEA) (530 µL, 3.0 mmol, 1.5 eq) in anhydrous DCM (15 mL). The reaction mixture was stirred at 0° C. for 30 min then at AT for 1 h30. At the end of reaction, the mixture was washed three times with a saturated aqueous solution of NaHCO₃ (3×20 mL). The organic phase was dried with Na₂SO₄, filtered and evaporated. The unrefined reaction medium was purified using silica gel column chromatography (eluent: petroleum ether:ethyl acetate/55:45/v:v) in order to obtain the compound 7 in the form of a viscous solid (500 mg, 1.16 mmol, yield: 46% over two stages).

¹H-NMR (500 MHz, CDCl₃): δ=7.27-7.06 (m, 10H), 6.12 (s, 1H), 4.08 (s, 1H), 3.43-3.36 (m, 3H), 3.21 (d, J=13.0 Hz, 1H), 2.61 (d, J=11.6 Hz, 1H), 2.57 (d, J=11.6 Hz, 1H), 1.99 (dd, J=11.6, 3.8 Hz, 1H), 1.92 (td, J=11.6, 3.8 Hz, 1H), 1.36 (s, 9H) ppm.

¹³C-NMR (125 MHz, CDCl₃): δ=171.0, 137.8, 135.1, 129.4, 128.9, 128.9, 128.8, 128.4, 127.3, 127.2, 80.1, 62.8, 54.2, 53.0, 49.7, 43.9, 41.0, 40.1, 28.5 ppm.

MS: ESI: [M+H]⁺ m/z found 424.3, calculated 424.3

R_f=0.23 (petroleum ether:ethyl acetate/6:4/v:v)

g) Preparation of Compound 8: N-((4-benzylpiperazin-2-yl)methyl)-2-phenylacetamide, in the Form of a Salt with Trifluoroacetic Acid

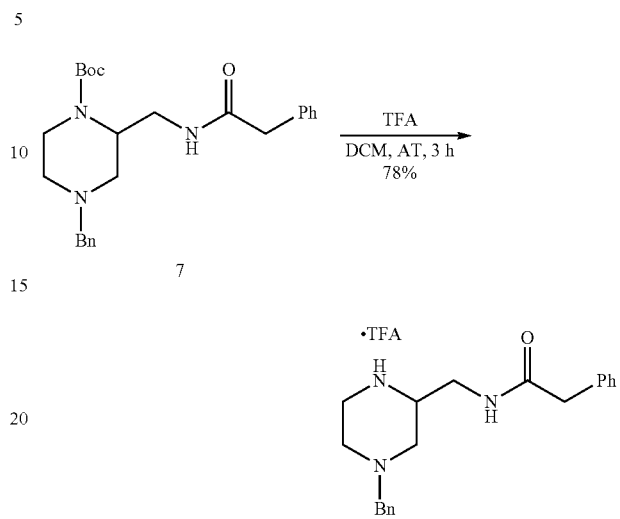

Trifluoroacetic acid (TFA) (4 mL) was added to a solution of compound 7 (500 mg, 1.18 mmol, 1.0 eq) in DCM (4 mL) and the reaction mixture was stirred at AT for 3 h. At the end of reaction, the reaction mixture was evaporated off under reduced pressure, redissolved in DCM and evaporated off once again. This operation was repeated two more times. The resulting oil was dissolved in MeOH and the product was precipitated from Et₂O. The suspension was filtered and dried in air in order to obtain the compound 8 in the form of a white powder (401 mg, 0.92 mmol, yield: 78%).

¹H-NMR (500 MHz, CD₃OD): δ=7.42-7.22 (m, 9H), 3.70-3.59 (m, 2H), 3.57 (s, 2H), 3.53-3.46 (m, 1H), 3.41-3.36 (m, 3H), 3.15 (td, J=11.3, 3.5 Hz, 1H), 2.98 (d, J=11.3 Hz, 2H), 2.44 (t, J=11.3 Hz, 1H), 2.24 (t, J=11.3 Hz, 1H) ppm.

¹³C-NMR (125 MHz, CD₃OD): δ=175.40, 136.40, 130.39, 130.26, 129.70, 129.62, 128.85, 128.13, 63.15, 56.87, 53.89, 50.29, 49.54, 44.80, 43.69, 40.74 ppm.

MS: ESI: [M+H]⁺ m/z found 324.3, calculated 324.3

II—Preparation of Intermediate 10: 4-methyl-2-oxo-2H-chromen-7-yl Carbonochloridate

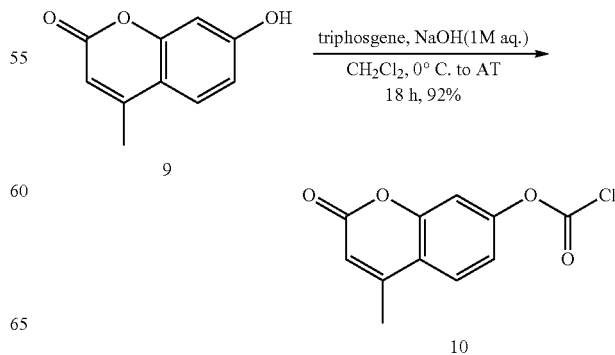

4. ethylumbelliferone 9 (360 mg, 2.0 mmol) was added to a solution, cooled to 0° C., of triphosgene (420 mg, 1.4 mmol, 0.7 eq) in DCM (10 mL) in a single portion. An aqueous solution of NaOH (2 M, 1.1 mL, 2.2 mmol, 1.1 eq) was added to this suspension dropwise and the reaction mixture was stirred at 0° C. for 1 h then at AT for 18 h. The suspension was then filtered and the resulting solid was washed twice with DCM and dried in air to provide approximately half of the expected mass of compound 10 (202 mg, 0.85 mmol). The filtrate was then washed twice with water and the organic phase was dried with $Na_2SO_4$, filtered and evaporated off to provide another portion of compound 10 (240 mg, 1.0 mmol) in the form of a white powder. The overall yield from this reaction was 93%.

$^1$H-NMR (300 MHz, $CDCl_3$): δ=7.69-7.62 (m, 1H), 7.33-7.19 (m, 2H), 6.31 (s, 1H), 2.46 (s, 3H,) ppm.

$R_f$=0.47 (cyclohexane: ethyl acetate/6:4/v:v)

III—Preparation of Compound 12, the Hydrochloride of 4-methyl-2-oxo-2H-chromen-7-yl 2-((2-phenylacetamido) methyl)piperazine-1-carboxylate

Example 1 a) Preparation of Compound 11: 4-methyl-2-oxo-2H-chromen-7-yl-4-benzyl-2-((2-phenylacetamido) methyl)piperazine-1-carboxylate

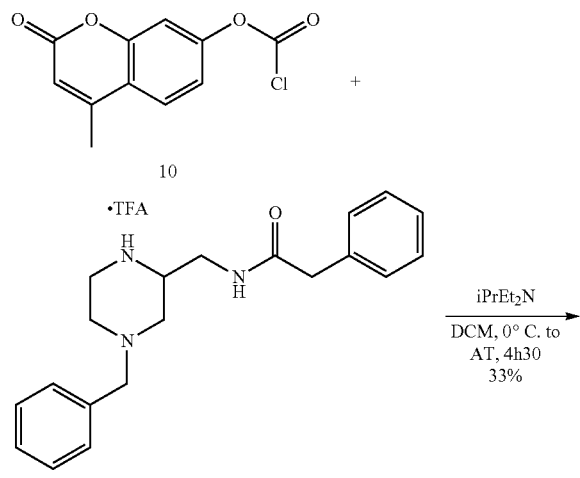

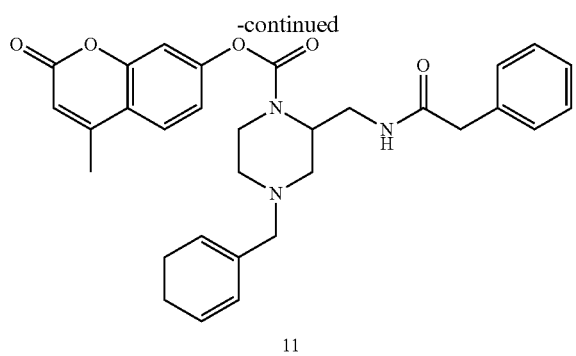

A solution of compound 8 (400 mg, 0.91 mmol, 1.0 eq) and DIPEA (480 μL, 2.73 mmol, 3.0 eq) in anhydrous DCM (5 mL) was added dropwise to a solution, cooled to 0° C., of compound 10 (230 mg, 0.96 mmol, 1.05 eq) in anhydrous DCM (10 mL) under an inert atmosphere of argon. The reaction mixture was then stirred at 0° C. for 30 min then at AT for 4 h. At the end of reaction, the reaction mixture was washed three times with a saturated aqueous solution of $NaHCO_3$ (3×20 mL) and the organic phase was dried with $Na_2SO_4$, filtered and evaporated off. The unrefined reaction medium was purified using silica gel column chromatography (eluent: gradient of DCM:MeOH/99:1, 98:2, 97:3/v:v) in order to obtain the compound 11 in the form of a colorless oil (160 mg, 0.31 mmol, yield: 33%).

$^1$H-NMR (500 MHz, $CDCl_3$): δ=7.46 (2×d, J=8.5 Hz, 1H), 7.26-7.06 (m, 10H), 7.02 (d, J=9.7 Hz, 1H), 6.97 (t, J=7.4 Hz, 1H), 6.25 (s, 0.5H), 6.13 (br s, 1H), 6.04 (s, 0.5H), 4.33 (s, 0.5H), 4.16 (s, 0.5H), 4.06-3.99 (m, 0.5H), 3.91 (t, J=13.2 Hz, 1H), 3.70-3.61 (m, 0.5H), 3.50-3.34 (m, 4H), 3.28 (t, J=12.6 Hz, 1H), 3.20-3.05 (m, 1H), 2.72 (d, J=11.9 Hz, 1H), 2.65 (d, J=11.8 Hz, 1H), 2.31 (d, J=7.7 Hz, 3H), 2.13 (dd, J=11.9, 4.0 Hz, 1H), 2.06 (t, J=11.8 Hz, 1H) ppm.

$^{13}$C-NMR (125 MHz, $CDCl_3$): δ=171.23, 160.68, 154.08, 153.82, 153.40, 152.76, 152.12, 137.53, 134.76, 129.38, 129.31, 128.90, 128.88, 128.44, 127.40, 127.24, 125.22, 118.11, 117.96, 117.37, 117.24, 114.20, 114.12, 110.29, 110.07, 62.63, 54.00, 53.85, 53.51, 52.74, 51.14, 43.79, 40.97, 40.46, 40.37, 18.72 ppm.

MS: ESI: [M+H]$^+$ m/z found 526.3, calculated 526.3

$R_f$=0.38 (DCM:MeOH/97:3/v:v)

b) Preparation of Compound 12: Hydrochloride of 4-methyl-2-oxo-2H-chromen-7-yl 2-((2-phenylacetamido)methyl)piperazine-1-carboxylate

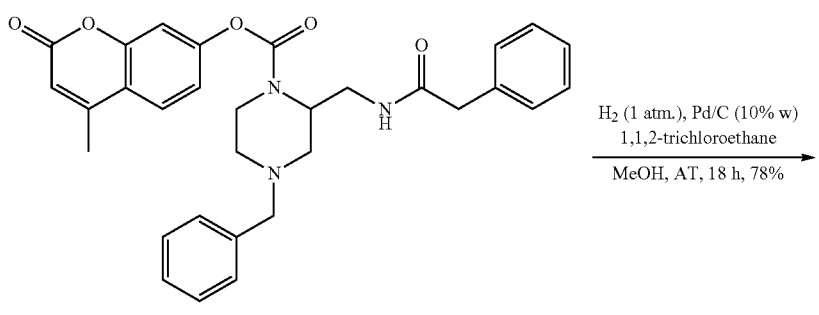

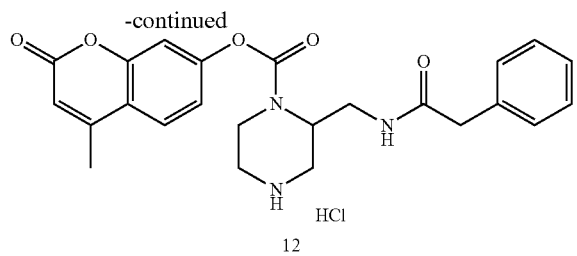

12

A flask containing a solution of compound 11 (120 mg, 0.23 mmol, 1.0 eq) and 1,1,2-trichloroethane (25 µL, 0.25 mmol, 1.1 eq) in MeOH (5 mL) was purged for 5 min with $H_2$. Pd/C (10%, 24 mg) was added and the flask was purged again with $H_2$ for 5 min. The reaction mixture was then stirred at AT for 18 h under an atmosphere of $H_2$. At the end of the reaction, the mixture was filtered over Celite® and the filtrate was evaporated off under reduced pressure to an approximate volume of 2 mL. $Et_2O$ was then added to precipitate out the product. The resulting suspension was filtered and dried in air to provide the compound 12 in the form of a white powder (85 mg, 0.18 mmol, yield: 78%).

$^1$H-NMR (500 MHz, CD$_3$OD): δ=7.80 (d, J=8.4 Hz, 1H), 7.35-7.07 (m, 7H), 6.33 (s, 1H), 4.63 (2×s, 1H), 4.33 (2×s, 1H), 3.78-3.66 (m, 1H), 3.53 (s, 3H), 3.45-3.32 (m, 3H), 3.21 (s, 1H), 2.49 (s, 3H) ppm.

$^{13}$C-NMR (125 MHz, CD$_3$OD): δ=175.07, 162.63, 155.25, 155.00, 136.46, 130.19, 129.71, 128.09, 127.15, 119.38, 119.02, 114.83, 111.09, 50.92, 50.42, 44.39, 44.04, 43.75, 38.60, 38.32, 37.44, 37.39, 18.72 ppm.

HRMS: $C_{24}H_{26}N_3O_5$ [M+H]$^+$ m/z found 436.1858, calculated 436.1867.

IV—Preparation of Intermediate 14, 2-phenyl-N-(piperidin-2-ylmethyl)acetamide

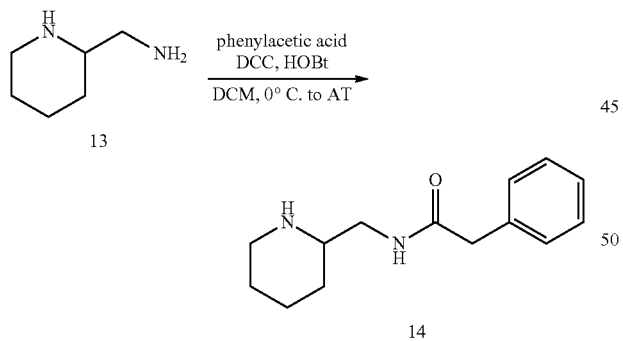

A solution of dicyclohexylcarbodiimide (2.56 g, 12.3 mmol, 1.1 eq) in DCM (10 mL) was added to a suspension of phenylacetic acid (1.54 g, 11.2 mmol, 1.0 eq) and HOBt (1.66 g, 12.3 mmol, 1.1 eq) in DCM (30 mL). The resulting mixture was stirred at AT for 30 min before adding 2-(aminomethyl)piperidine 13 (1.4 mL, 11.2 mmol, 1.0 eq). The reaction mixture was then stirred at AT for 2 h. The resulting suspension was filtered and the filtrate was washed twice with a saturated aqueous solution of NaHCO$_3$ (2×50 mL). The organic phase was then extracted several times with an aqueous 10% solution of KH$_2$PO$_4$ until the pH of the aqueous phase was stable at about a pH of 3. DCM (150 mL) was then added to the combined aqueous phases and an aqueous solution of NaOH (2 M) was added until the pH of the aqueous phase reached a pH of 12. The organic phase was extracted and the basic aqueous phase was extracted twice with DCM (2×100 mL). The organic phases were combined, dried with Na$_2$SO$_4$, filtered and evaporated off to provide the compound 14 in the form of a white solid (2.07 g, 8.9 mmol, yield: 80%).

$^1$H-NMR (200 MHz, CDCl$_3$): δ=7.83 (m, 5H), 5.80 (s, 1H), 3.57 (s, 2H), 3.25 (m, 1H), 3.04 (m, 2H), 2.59 (m, 2H), 1.75 (m, 1H), 1.56 (m, 2H), 1.32 (m, 4H), 1.03 (m, 1H) ppm.

MS: ESI: [M+H]$^+$ m/z found 233.3, calculated 233.3

V—Preparation of Compound 15, 4-methyl-2-oxo-2H-chromen-7-yl 2-((2-phenylacetamido)methyl)piperidine-1-carboxylate (Comparative 1)

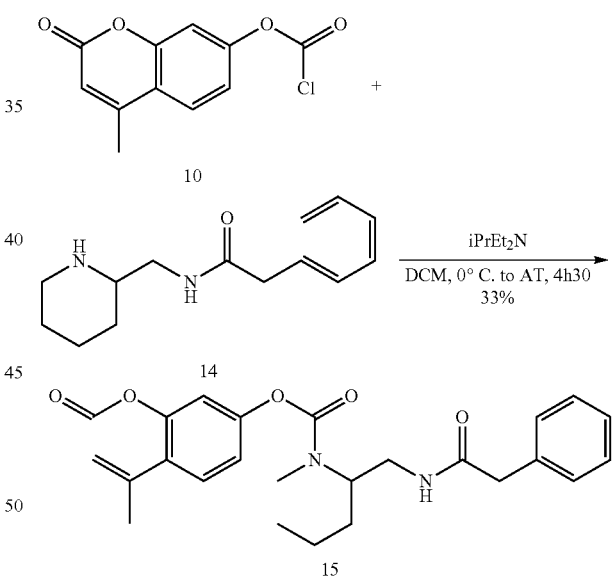

Compound 14 (25 mg, 0.15 mmol, 1.0 eq) followed by DIPEA (55 µL, 0.30 mmol, 2.0 eq) was added to a suspension, cooled to 0° C., of compound 10 (39 mg, 0.16 mmol, 1.05 eq) in anhydrous DCM (5 mL) under an inert atmosphere of argon. The reaction mixture was stirred at 0° C. for 30 min and at AT for 4 h. At the end of the reaction, the reaction mixture was washed three times with a saturated aqueous solution of NaHCO$_3$ (3×20 mL) and the organic phase was dried with Na$_2$SO$_4$, filtered and evaporated. The unrefined reaction medium was purified using silica gel column chromatography (eluent: gradient of DCM:MeOH/ 99:1, 98:2, 97:3/v:v) in order to obtain the compound 15 in the form of a colorless oil (35 mg, 0.31 mmol, yield: 54%).

$^1$H-NMR (500 MHz, CDCl$_3$): δ=7.49 (s, 1H), 7.30-7.04 (m, 5H), 7.04-6.88 (m, 2H), 6.16 (s, 1H), 5.90 (s, 1H), 4.48-4.23 (m, 1H), 4.03 (d, J=13.5 Hz, 1H), 3.82 (s, 1H), 3.64-3.27 (m, 3H), 3.12 (s, 1H), 2.35 (s, 3H), 1.77-1.36 (m, 6H) ppm.

$^{13}$C-NMR (125 MHz, CDCl$_3$): δ=171.42, 160.73, 154.14, 153.99, 153.83, 152.12, 134.62, 129.75, 129.36, 129.00, 128.38, 127.35, 126.76, 125.19, 118.10, 117.32, 114.20, 110.34, 53.51, 51.09, 50.93, 46.72, 43.69, 41.28, 40.83, 40.64, 39.53, 38.94, 31.69, 26.53, 25.28, 24.39, 23.04, 19.09, 18.76 ppm.

HRMS: C$_{25}$H$_{26}$N$_2$NaO$_5$ [M+Na]$^+$ m/z found 457.1734, calculated 457.1734

R$_f$=0.27 (DCM:MeOH/98:2/v:v)

VI—Preparation of Intermediate 19, (4-benzylpiperazin-2-yl)methyl Octanoate in the Form of a Salt with Trifluoroacetic Acid a) Preparation of Compound 17: Octanoyl Chloride

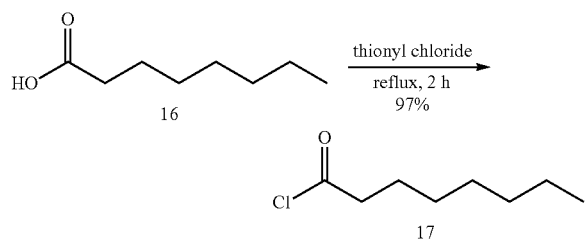

Thionyl chloride (30 mL, 410 mmol, 6.0 eq) was added dropwise to octanoic acid 16 (10.0 g, 69 mmol, 1.0 eq). This reaction mixture was then heated under reflux for 2 h, then cooled to AT and the volatile compounds were evaporated off under reduced pressure. The resulting oil was taken up in DCM and the solution was evaporated once more. This procedure was carried out again two more times in order to obtain the compound 17 in the form of a highly odorous yellow liquid (11.0 g, 66.7 mmol, yield: 97%).

$^1$H-NMR (300 MHz, CDCl$_3$): δ=2.87 (t, J=7.3 Hz, 2H), 1.70 (q, J=7.3 Hz, 2H), 1.42-1.22 (m, 8H), 0.88 (t, J=6.6 Hz, 3H) ppm.

$^{13}$C-NMR (75 MHz, CDCl$_3$) δ=173.89, 47.23, 31.64, 28.85, 28.51, 25.20, 22.65, 14.11 ppm.

b) Preparation of Compound 18: tert-butyl 4-benzyl-2-((octanoyloxy)methyl)piperazine-1-carboxylate

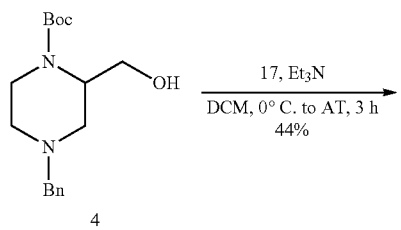

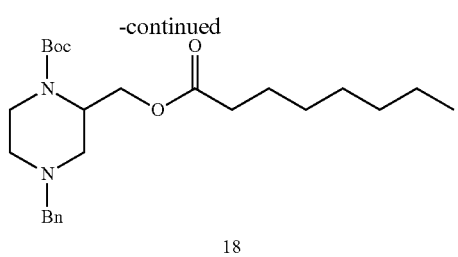

A solution of compound 17 (667 mg; 4.1 mmol, 1.1 eq) in anhydrous DCM (5 mL) was added dropwise to a solution, cooled to 0° C., of compound 4 (800 mg, 3.72 mmol, 1.0 eq) and triethylamine (780 μL, 5.6 mmol, 1.5 eq) in anhydrous DCM (10 mL). The reaction mixture was stirred at 0° C. for 30 min then at AT for 2 h30. It was then diluted with DCM (35 mL) and washed once with a saturated aqueous solution of NaHCO$_3$ (50 mL), once with of water (50 mL), once with an aqueous solution of HCl (1 M-50 mL) and once with brine (50 mL). The organic phase was dried with Na$_2$SO$_4$, filtered and evaporated off. The unrefined reaction medium was purified using silica gel column chromatography (pure DCM, then DCM:ethyl acetate/90:10) to obtain 18 in the form of a yellow oil (710 mg, 1.64 mmol, yield: 44%).

$^1$H-NMR (500 MHz, CD$_3$OD): δ=7.34-7.16 (m, 5H), 4.39-4.18 (m, 3H), 3.88 (s, 1H), 3.53 (d, J=13.1 Hz, 1H), 3.37 (d, J=13.1 Hz, 1H), 3.09 (t, J=11.3 Hz, 1H), 2.77 (d, J=11.5 Hz, 2H), 2.20 (t, J=7.6 Hz, 2H), 2.14-1.95 (m, 2H), 1.60-1.49 (m, 2H), 1.44 (s, 9H), 1.25 (s, 8H), 0.87 (t, J=6.4 Hz, 3H) ppm.

$^{13}$C-NMR (125 MHz, CD$_3$OD): δ=173.72, 154.91, 138.16, 128.93, 128.42, 127.29, 79.97, 62.83, 61.56, 53.10, 52.82, 34.36, 31.80, 29.25, 29.04, 28.52, 24.95, 22.73, 14.20 ppm.

MS: ESI: [M+H]$^+$ m/z found 433.3, calculated 433.3 c) Preparation of Compound 19: (4-benzylpiperazin-2-yl)methyl Octanoate in the Form of a Salt with Trifluoroacetic Acid

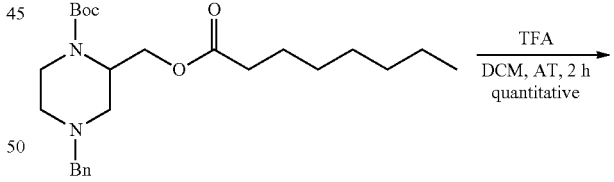

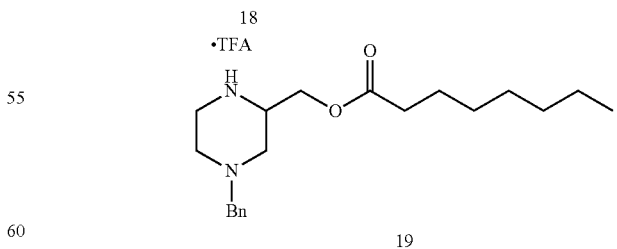

The procedure used was the same as that described for the synthesis of compound 8, but using the compound 18 (700 mg, 1.62 mmol. 0 eq) in DCM (5 mL) and TFA (5 mL) in order to provide the compound 19 in the form of a white powder (775 mg, yield: quantitative).

¹H-NMR (500 MHz, CD₃OD): δ=7.41-7.27 (m, 5H), 4.30 (dd, J=12.5, 3.9 Hz, 1H), 4.22 (dd, J=12.5, 6.4 Hz, 1H), 3.70-3.63 (m, 1H), 3.46 (d, J=13.2 Hz, 1H), 3.28-3.12 (m, 3H), 2.71 (td, J=12.2, 12.2, 2.6 Hz, 1H), 2.61 (t, J=11.8 Hz, 1H), 2.38 (t, J=7.5 Hz, 2H), 1.66-1.52 (m, 2H), 1.30 (s, 8H), 0.89 (t, J=6.7 Hz, 3H) ppm.

¹³C-NMR (125 MHz, CD₃OD): δ=174.57, 162.06, 161.77, 135.40, 130.95, 129.86, 129.62, 118.70, 116.40, 62.75, 62.55, 54.98, 52.20, 49.86, 43.97, 34.47, 32.84, 30.13, 30.07, 25.72, 23.65, 14.38 ppm.

MS: ESI: [M+H]⁺ m/z found 333.3, calculated 333.2

VII—Preparation of Compound 21, the Hydrochloride of 4-methyl-2-oxo-2H-chromen-7-yl 2-((octanoyloxy)methyl)piperazine-1-carboxylate

EXAMPLE 2 a) Preparation of Compound 20: 4-methyl-2-oxo-2H-chromen-7-yl 4-benzyl-2-((octanoyloxy)methyl)piperazine-1-carboxylate

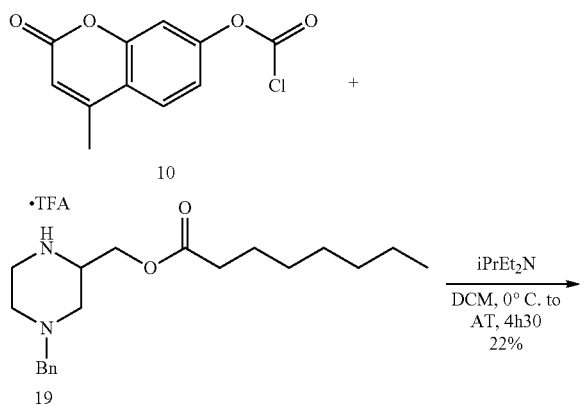

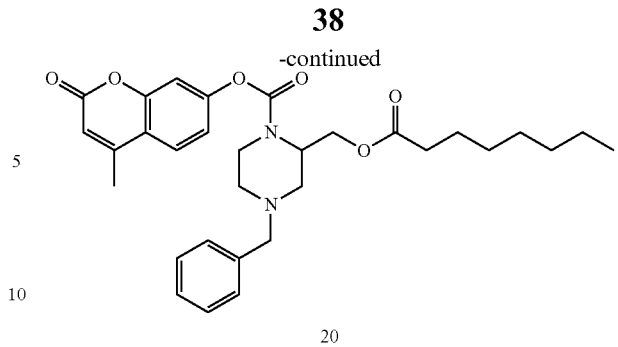

20

The procedure used was the same as that described for the synthesis of compound 11, with compound 10 (400 mg, 1.67 mmol, 1.0 eq), compound 19 (750 mg, 1.67 mmol, 1.0 eq) and DIPEA (880 μL, 5.02 mmol, 3.0 eq) in anhydrous DCM (20 mL). Following silica gel chromatography (petroleum ether:ethyl acetate/7:3/v:v), the compound 20 was obtained in the form of a colorless solid (190 mg, 0.36 mmol, yield: 22%).

¹H-NMR (500 MHz, CD₃OD): δ=7.52 (d, J=8.6 Hz, 1H), 7.24-7.16 (m, 1H), 7.11-7.00 (m, 2H), 6.18 (s, 1H), 4.57-4.38 (m, 2H), 4.27 (s, 1H), 4.09-3.95 (m, 1H), 3.54 (d, J=13.1 Hz, 1H), 3.39 (d, J=13.0 Hz, 1H), 3.23 (t, J=11.9 Hz, 0.5H), 2.82 (d, J=11.3 Hz, 2H), 2.36 (s, 3H), 2.21-2.10 (m, 3H), 1.55-1.43 (m, 2H), 1.26-1.12 (m, 8H), 0.87-0.75 (m, 3H) ppm.

¹³C-NMR (125 MHz, CD₃OD): a 173.46, 160.56, 154.10, 153.82, 152.88, 152.00, 137.65, 128.76, 128.35, 127.29, 125.17, 118.11, 117.90, 117.29, 114.14, 110.25, 110.05, 62.57, 61.57, 61.28, 52.75, 52.62, 51.16, 50.57, 41.02, 40.21, 34.13, 31.58, 29.03, 28.86, 24.76, 22.54, 18.65, 14.03 ppm.

MS: ESI: [M+H]⁺ m/z found 535.3, calculated 535.3
$R_f$=0.26 (petroleum ether:ethyl acetate/7:3/v:v)

b) Preparation of Compound 21: Hydrochloride of 4-methyl-2-oxo-2H-chromen-7-yl 2-((octanoyloxy)methyl)piperazine-1-carboxylate

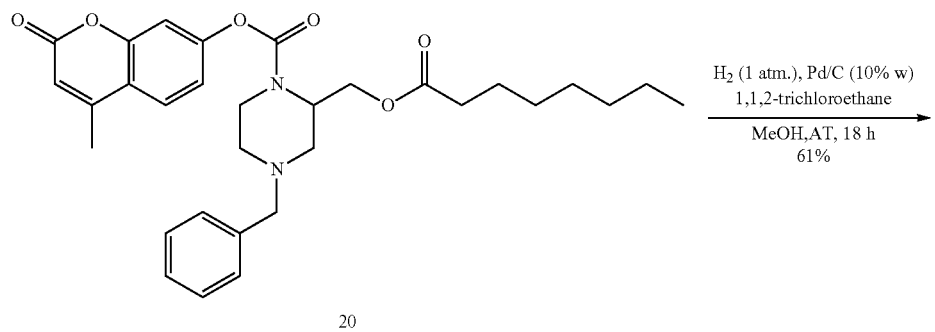

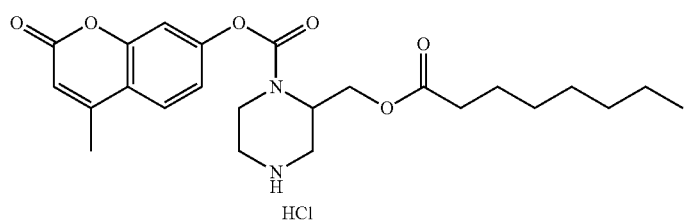

The procedure used was the same as that described for the synthesis of compound 12, with compound 20 (180 mg, 0.33 mmol, 1.0 eq), 1,1,2-trichloroethane (37 μL, 0.39 mmol, 1.1 eq), Pd/C (38 mg, 20% w) in MeOH (5 mL) in order to obtain the compound 21 in the form of a white powder (95 mg, 0.20 mmol, yield: 61%).

$^{1}$H-NMR (500 MHz, CD$_3$OD): δ=7.82 (d, J=8.6 Hz, 1H), 7.32-7.13 (m, 2H), 6.34 (s, 1H), 4.67 (s, 1H), 4.43-4.22 (m, 2H), 3.53 (d, J=13.4 Hz, 2H), 3.45 (d, J=11.7 Hz, 3H), 3.26 (s, 1H), 2.49 (s, 3H), 2.35 (t, J=7.5 Hz, 2H), 1.57 (s, 2H), 1.26 (dd, J=28.7, 21.9 Hz, 9H), 0.84 (t, J=6.8 Hz, 3H) ppm.

$^{13}$C-NMR (125 MHz, CD$_3$OD): δ=174.84, 162.51, 155.27, 154.96, 154.90, 154.05, 127.20, 119.25, 119.06, 114.87, 111.01, 61.14, 43.94, 43.50, 34.83, 32.80, 30.17, 30.07, 25.89, 23.63, 18.67, 14.36 ppm.

HRMS: C$_{24}$H$_{33}$N$_2$O$_6$ [M+H]$^+$ m/z found 445.2318, calculated 445.2333

VIII—Preparation of Compound 22, 4-(4-(((4-methyl-2-oxo-2H-chromen-7-yl)oxy)carbonyl)-3-((octanoyloxy)methyl)piperazin-1-yl)butane-1-sulfonic Acid

EXAMPLE 3

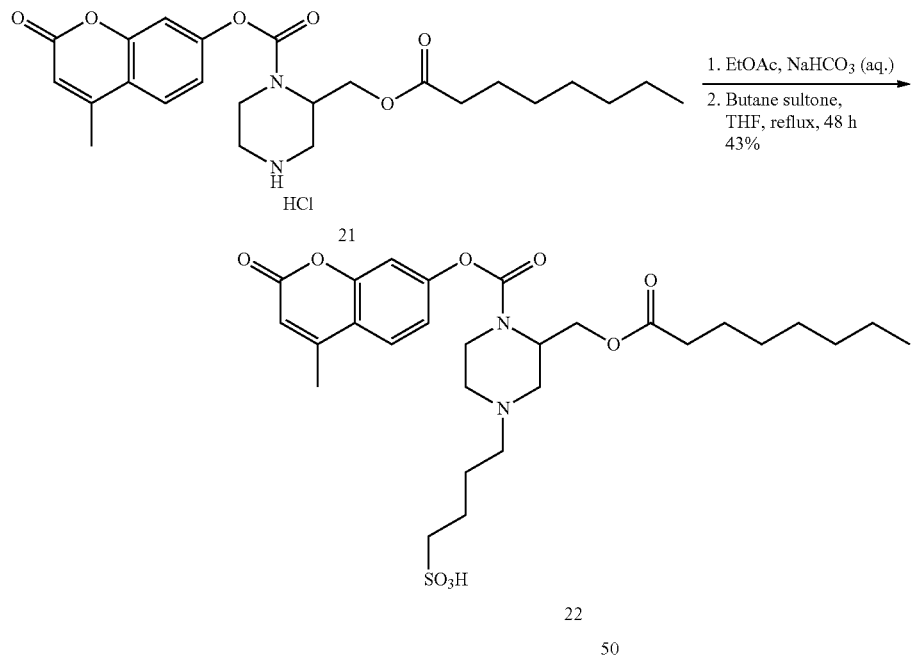

An aqueous solution of NaHCO (1 M, 10 mL) was added to a suspension of compound 21 (25 mg, 0.052 mmol, 1.0 eq) in ethyl acetate (10 mL). The organic phase was extracted and the aqueous phase was washed three times with ethyl acetate (3×10 mL). The combined organic phases were dried with Na$_2$SO$_4$, filtered and evaporated off to provide a colorless oil. This oil was dissolved in anhydrous THF (2.5 mL), and butane sultone was added (2 drops) and the reaction mixture was heated under reflux for 48 h. At the end of the reaction, it was diluted with THF (2.5 mL) and Et$_2$O (5 mL) and water was added (10 mL). The aqueous phase was separated out and freeze dried in order to provide the compound 22 in the form of a white, highly hygroscopic solid (13 mg, 0.022 mmol, yield: 43%).

$^{1}$H-NMR (500 MHz, CD$_3$OD): δ=7.72 (d, J=8.6 Hz, 1H), 7.21-7.03 (m, 2H), 6.23 (d, J=1.1 Hz, 1H), 4.59 (s, 1H), 4.38-4.12 (m, 2H), 3.62-3.24 (m, 4H), 3.12-2.83 (m, 3H), 2.80 (t, J=6.9 Hz, 2H), 2.42-2.35 (m, 3H), 2.29-2.17 (m, 2H), 1.91-1.73 (m, 4H), 1.47 (s, 2H), 1.25-0.98 (m, 10H), 0.74 (t, J=6.9 Hz, 3H) ppm.

$^{13}$C-NMR (125 MHz, CD$_3$OD): δ=162.54, 155.30, 155.02, 154.93, 127.23, 119.30, 118.88, 114.88, 34.89, 32.83, 30.21, 30.10, 25.92, 23.67, 23.24, 18.71, 14.40 ppm.

HRMS: C$_{28}$H$_{40}$N$_2$NaO$_9$S [M+Na]$^+$ m/z found 603.2339, calculated 603.2347

IX—Preparation of Compound 27, 4-methyl-2-oxo-2H-chromen-7-yl 2-((octanoyloxy)methyl)piperidine-1-carboxylate (Comparative 2) a) Preparation of Compound 24: N-Boc-2-(hydroxymethyl)piperidine

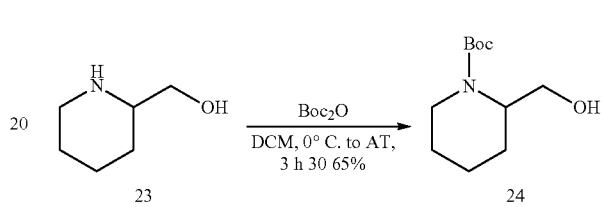

A solution of Boc$_2$O (6.6 g, 47 mmol, 1.1 eq) in DCM (10 mL) was added dropwise to a solution, cooled to 0° C., of compound 23 (5 g, 43 mmol, 1.0 eq) in DCM (20 mL). The reaction mixture was stirred at 0° C. for 30 min, then at AT for 3 h. It was then diluted with DCM (30 mL) and washed once with a saturated aqueous solution of NaHCO$_3$ (3×60 mL). The organic phase was dried with Na$_2$SO$_4$, filtered and evaporated off in order to obtain the compound 24 (6.02 g, 28 mmol, yield: 65%) in the form of a yellow solid.

$^{1}$H-NMR (300 MHz, CDCl$_3$) δ=4.36-4.22 (m, 1H), 3.94 (d, J=12.3 Hz, 1H), 3.88-3.75 (m, 1H), 3.67-3.53 (m, 1H), 2.87 (t, J=12.3 Hz, 1H), 2.01 (br s, 1H), 1.73-1.52 (m, 4H), 1.52-1.38 (m, 11H) ppm.

$^{13}$C-NMR (75 MHz, CDCl$_3$) δ=156.43, 79.92, 61.86, 52.68, 40.14, 28.57, 25.39, 25.35, 19.76 ppm.

b) Preparation of Compound 25: N-Boc-2-((octanoyloxy)methyl)piperidine

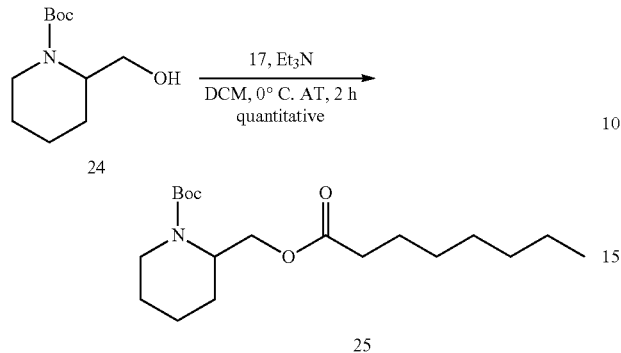

A solution of compound 24 (5.0 g, 30.6 mmol, 1.1 eq) in dry DCM (20 mL) was added dropwise to a solution, cooled to 0° C., of compound 17 (6.0 g, 27.8 mmol, 1.0 eq) and triethylamine (6 mL, 42 mmol, 1.5 eq) in DCM sec (40 mL). The reaction mixture was stirred at 0° C. for 30 min and at AT for 3 h. It was then diluted with DCM (40 mL) and washed once with 1 M HCl (100 mL), once with water (50 mL), once with NaOH 1 M (100 mL), and once with brine (100 mL). The organic phase was dried with $Na_2SO_4$, filtered and evaporated off to dryness to provide the compound 25 (9.82 g, quantitative yield) in the form of a yellow liquid used without further purification.

$^1$H-NMR (300 MHz, $CDCl_3$) δ=4.40 (s, 0.6H), 4.26-4.11 (m, 0.9H), 4.10-3.99 (m, 1.3H), 3.99-3.80 (m, 0.8H), 3.76-3.64 (m, 0.2H), 3.59-3.47 (m, 0.2H), 2.86-2.65 (m, 0.8H), 2.48 (s, 0.2H), 2.37 (t, J=7.5 Hz, 0.2H), 2.21 (t, J=7.5 Hz, 2H), 1.68-1.43 (m, 6H), 1.43-1.30 (m, 9H), 1.30-1.08 (m, 10H), 0.80 (t, J=5.9 Hz, 3H) ppm.

$^{13}$C-NMR (75 MHz, $CDCl_3$) δ=173.77, 155.15, 79.54, 61.71, 34.38, 31.75, 29.21, 28.99, 28.52, 25.50, 25.35, 24.98, 22.67, 19.42, 14.13 ppm.

c) Preparation of Compound 26: piperidine-2-ylmethyl octanoate in the Form of a Salt with Trifluoroacetic Acid

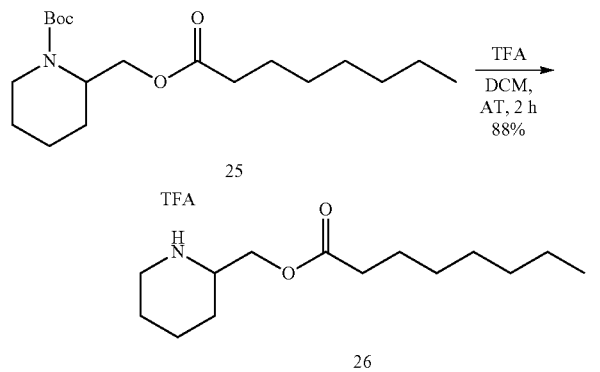

The procedure used was the same as that described for the synthesis of compound 8, but using the compound 25 (700 mg, 1.62 mmol, 1.0 eq) in DCM (3 mL) and TFA (3 mL) in order to provide the compound 26 in the form of a white powder (910 mg, 2.56 mmol, yield: 88%).

$^1$H-NMR (300 MHz, $CDCl_3$) δ=8.93 (s, 1H), 8.25 (s, 1H), 4.54 (d, J=5.4 Hz, 0.1H), 4.32 (d, J=3.4 Hz, 0.3H), 4.28 (d, J=3.4 Hz, 0.6H), 4.23-4.07 (m, 1H), 3.50 (d, J=12.7 Hz, 1H), 3.43-3.26 (m, 1H), 3.03-2.83 (m, 1H), 2.30 (t, J=7.6 Hz, 1H), 2.06-1.46 (m, 8H), 1.39-1.17 (m, 9H), 0.87 (t, J=5.7 Hz, 3H) ppm.

$^{13}$C-NMR (75 MHz, $CDCl_3$) δ=173.81, 161.67, 117.60, 63.67, 56.40, 45.11, 33.69, 31.71, 29.06, 28.95, 25.16, 24.67, 22.66, 22.06, 21.97, 14.10 ppm.

MS: ESI: $[M+H]^+$ m/z found 241.2, calculated 241.2 d) Preparation of Compound 27: 4-methyl-2-oxo-2H-chromen-7-yl 2-((octanoyloxy)methyl)piperidine-1-carboxylate

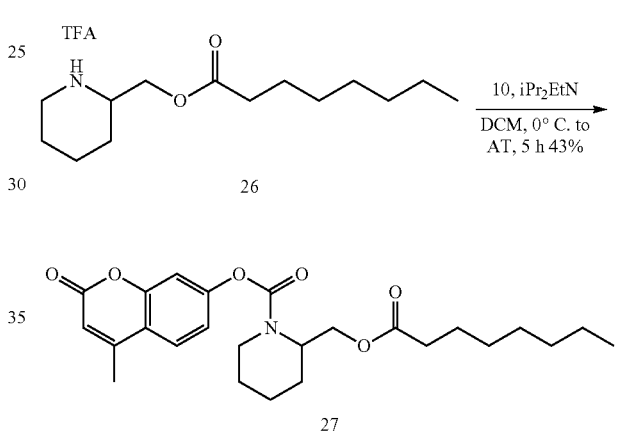

The procedure used was the same as that described for the synthesis of compound 11, with compound 10 (190 mg, 0.79 mmol, 1.0 eq), compound 26 (285 mg, 0.79 mmol, 1.0 eq) and DIPEA (700 μL, 3.95 mmol, 4.0 eq) in anhydrous DCM (10 mL). Following silica gel chromatography (petroleum ether:ethyl acetate/75:25/v:v), the compound 27 was obtained in the form of a colorless oil (150 mg, 0.34 mol, yield 43%).

$^1$H-NMR (500 MHz, $CDCl_3$) δ=7.57 (d, J=8.6 Hz, 1H), 7.16-7.05 (m, 2H), 6.24 (s, 1H), 4.68 (s, 1H), 4.41 (t, J=9.9 Hz, 1H), 4.22-4.10 (m, 2H), 3.13 (br s, 0.5H), 2.98 (br s, 0.5H), 2.42 (s, 3H), 2.28 (t, J=6.8 Hz, 2H), 1.85-1.66 (m, 4H), 1.65-1.50 (m, 4H), 1.24 (br s, 8H), 0.84 (t, J=6.6 Hz, 3H) ppm.

$^{13}$C-NMR (125 MHz, $CDCl_3$) δ=173.77, 160.82, 154.33, 154.20, 153.29, 152.12, 125.22, 118.25, 117.39, 114.31, 110.39, 61.67, 50.35, 50.00, 40.89, 40.09, 34.37, 31.75, 29.22, 29.03, 25.81, 25.12, 24.99, 22.70, 19.32, 18.85, 14.17 ppm.

HRMS: $C_{25}H_{33}NNaO_6$ $[M+Na]^+$ m/z found: 466.2179, calculated 466.200

$R_f$=0.34 (petroleum ether:ethyl acetate/75:25/v:v)

X—Preparation of Compound 31, 4-methyl-2-oxo-2H-chromen-7-yl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

EXAMPLE 4 a) Preparation of Compound 29, 1-azido-2-(2-(2-methoxyethoxy)ethoxy)ethane

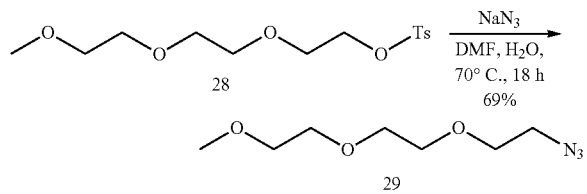

NaN$_3$ (2.04 g, 31.40 mmol, 5.0 eq) was added in a single portion to a solution of compound 28 (2.0 g, 6.28 mmol, 1.0 eq) in a mixture of DMF (15 mL) and water (8 mL). This reaction mixture was then heated to 70° C. for 18 h. The volatile compounds were then evaporated off and the resulting solid was taken up in ethyl acetate (50 mL). The suspension was filtered and the filtrate was washed twice with a saturated aqueous solution of NaHCO$_3$ (2×50 mL), then once with brine (50 mL). The organic phase was dried with Na$_2$SO$_4$, filtered and evaporated off to provide the compound 29 in the form of a colorless oil (820 mg, 4.33 mmol, yield: 69%).

$^1$H-NMR (300 MHz, CDCl$_3$) δ=3.68-3.57 (m, 8H), 3.55-3.48 (m, 2H), 3.38-3.32 (m, 5H) ppm.

$^{13}$C-NMR (75 MHz, CDCl$_3$) δ=71.94, 70.71, 70.68, 70.63, 70.05, 59.04, 50.69 ppm.

R$_f$=0.56 (petroleum ether:ethyl acetate/1:1/v:v)

b) Preparation of Compound 30, 4-methyl-2-oxo-2H-chromen-7-yl 4-(pent-4-ynoyl)-2-((2-phenylacetamido)methyl)piperazine-1-carboxylate

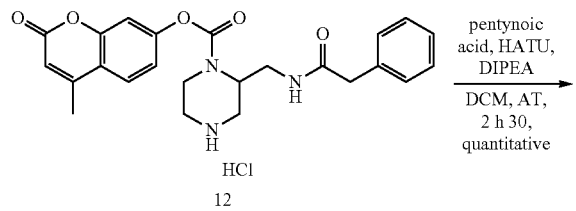

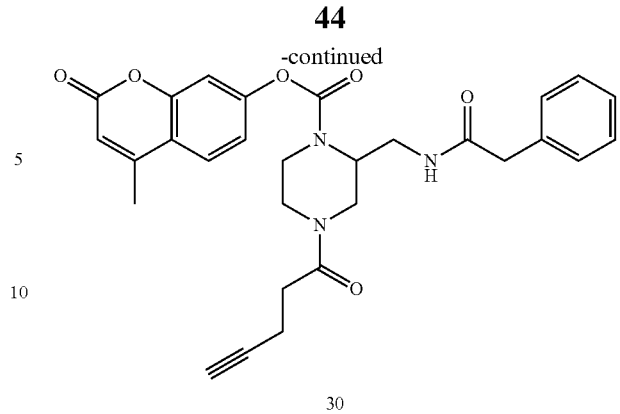

DIPEA (42 µL, 0.240 mmol, 2.2 eq) was added to a suspension of compound 12 (50 mg, 0.106 mmol, 1.0 eq), pentynoic acid (12 mg, 0.117 mmol, 1.1 eq) and HATU (46 mg, 0.117 mmol, 1.1 eq) in anhydrous DCM (5 mL) under an inert atmosphere of argon, and the reaction mixture was stirred at AT for 2 h30. At the end of the reaction, the reaction mixture was diluted with DCM (20 mL) and washed twice with a saturated aqueous solution of NaHCO$_3$ (2×20 mL) and once with brine (20 mL). The organic phase was dried with Na$_2$SO$_4$, filtered and evaporated. The unrefined reaction medium was purified by column chromatography over neutral alumina (petroleum ether:ethyl acetate/ 1:9/v:v) in order to obtain the compound 30 in the form of a colorless oil (60 mg, yield: quantitative).

$^1$H-NMR (500 MHz, CDCl$_3$) δ=7.59 (dd, J=14.8, 8.6 Hz, 1H), 7.36-7.27 (m, 2H), 7.27-7.21 (m, 2H), 7.21-7.02 (m, 2H), 6.73-6.45 (m, 1H), 6.32-6.04 (m, 1H), 4.67-4.25 (m, 2H), 4.17-3.69 (m, 3H), 3.66-3.47 (m, 3H), 3.45-3.18 (m, 2H), 3.18-2.89 (m, 2H), 2.81 (s, 3H), 2.74-2.63 (m, 1H), 2.60-2.47 (m, 3H), 2.44 (s, 3H), 2.20 (s, 1H), 2.13-1.96 (m, 1H) ppm.

$^{13}$C-NMR (125 MHz, CDCl$_3$) δ=171.52, 171.36, 170.69, 170.37, 170.27, 165.73, 160.62, 154.03, 153.52, 153.23, 152.78, 152.16, 134.78, 134.65, 129.23, 128.97, 128.88, 127.33, 127.21, 125.35, 117.97, 117.58, 117.45, 114.33, 114.22, 110.28, 110.16, 83.32, 83.05, 69.34, 69.03, 53.52, 51.33, 45.59, 45.20, 45.03, 43.62, 42.37, 42.19, 41.21, 40.48, 40.19, 39.98, 38.62, 38.05, 37.50, 31.77, 18.74, 14.66, 14.36 ppm.

MS: ESI: [M+H]$^+$ m/z found 515.3, calculated 515.2

R$_f$=0.20 (petroleum ether:ethyl acetate/1:9/v:v)

c) Preparation of Compound 31, 4-methyl-2-oxo-2H-chromen-7-yl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

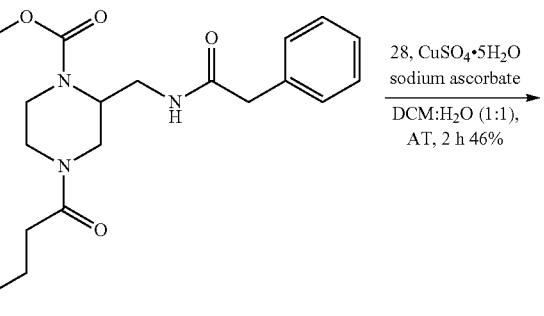

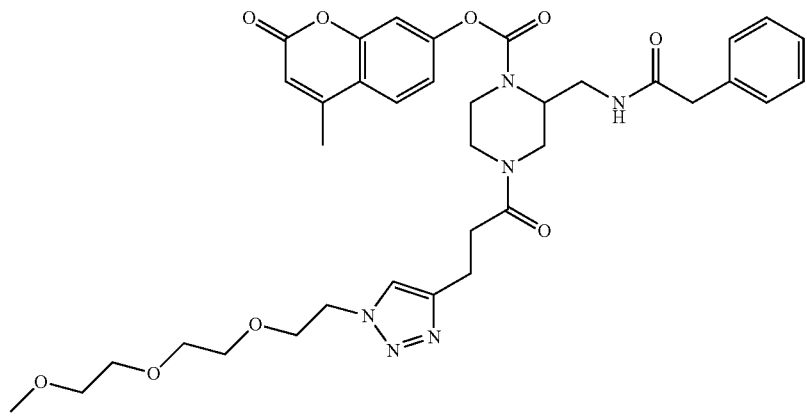

31

CuSO$_4$.5H$_2$O (9 mg, 0.04 mmol, 0.6 eq) and sodium ascorbate (16 mg, 0.08 mmol, 1.2 eq) were added in a single portion to a solution of compound 30 (30 mg, 0.058 mmol, 1.0 eq) and compound 28 (24 mg, 0.128 mmol, 2.2 eq) in a mixture of DCM (1 mL) and water (1 mL). This reaction mixture was then stirred at AT for 2 h. At the end of the reaction, the reaction mixture was diluted with DCM (10 mL) and water (10 mL). The organic phase was extracted and the aqueous phase was washed three times with DCM (3×10 mL). The combined organic phases were dried with Na$_2$SO$_4$, filtered and evaporated off. The unrefined reaction medium was purified using silica gel column chromatography (eluent: gradient of DCM:MeOH/100: 0, 99:1, 98:2, 97:3, 96:4, 95:5/v:v) in order to provide the compound 31 in the form of a white powder (19 mg, 0.027 mmol, yield: 46%).

$^1$H-NMR (500 MHz, CDCl$_3$) δ=7.96 (s, 0.25H), 7.47 (m 1.5H), 7.32-6.94 (m, 7H), 6.61 (s, 0.2H), 6.21 (m, 1H), 5.86 (s, 0.2H), 4.73 (s, 0.25H), 4.55-4.17 (m, 3H), 4.01-3.69 (m, 4.5H), 3.65-3.61 (m, 1.5H), 3.59-3.50 (m, 6.5H), 3.50-3.38 (m, 3H), 3.31 (d, J=5.4 Hz, 2.5H), 3.26-2.55 (m, 6.5H), 2.36 (s, 3H), 1.74 (s, 1H) ppm.

$^{13}$C-NMR (125 MHz, CDCl$_3$) δ=172.66, 171.54, 170.71, 160.77, 154.23, 153.64, 152.93, 152.10, 135.49, 134.96, 134.70, 129.42, 129.03, 128.85, 127.35, 127.14, 125.36, 122.96, 118.17, 117.60, 114.42, 110.45, 72.04, 70.64, 69.56, 67.21, 59.18, 51.27, 50.71, 50.21, 45.48, 45.21, 44.77, 44.02, 43.86, 42.43, 42.22, 41.15, 40.55, 40.24, 40.00, 39.36, 38.12, 37.72, 37.42, 32.04, 31.66, 29.81, 28.81, 21.34, 20.57, 18.86 ppm.

MS: ESI: [M+H]$^+$ m/z found 704.5, calculated 704.3

R$_f$=0.30 (DCM:MeOH/95:5/v:v)

XI—Preparation of Intermediate 34, N-((4-(pent-4-ynoyl)piperazin-2-yl)methyl)-2-phenylacetamide in the Form of a Salt with Trifluoroacetic Acid a) Preparation of Compound 32, tert-butyl 2-((2-phenylacetamido)methyl)piperazine-1-carboxylate, Hydrochloride Salt

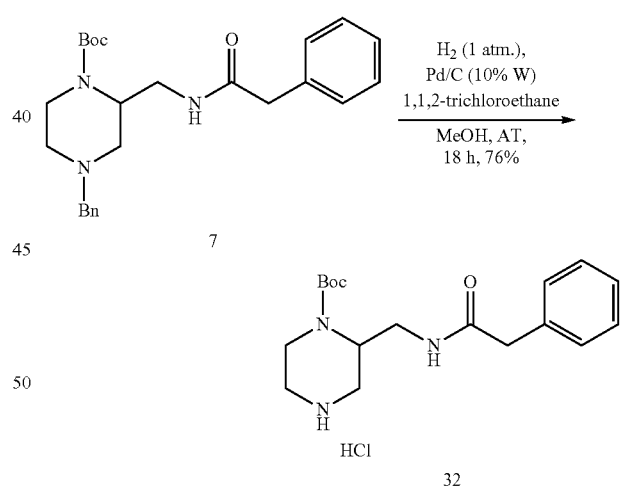

The procedure used was the same as that described for the synthesis of compound 12, with the compound 7 (605 mg, 1.53 mmol, 1.0 eq), 1,1,2-trichloroethane (161 μL, 1.70 mmol, 1.1 eq), Pd/C (121 mg, 20% by weight) in MeOH (30 mL) in order to obtain the compound 32 in the form of a white powder (430 mg, 1.16 mmol, yield: 76%).

$^1$H-NMR (300 MHz, CDCl$_3$) δ=7.43-7.15 (m, 5H), 6.25 (s, 1H), 4.47-4.15 (m, 2H), 4.00-3.57 (m, 2.7H), 3.52 (d, J=2.9 Hz, 2H), 3.33 (m, 0.7H), 3.28-2.85 (m, 2.8H), 2.68-2.29 (m, 4.5H), 2.00 (d, J=8.4 Hz, 1H), 1.47 (s, 9H) ppm.

$^{13}$C-NMR (75 MHz, CDCl$_3$) δ=171.53, 171.33, 170.51, 170.26, 165.70, 154.91, 134.84, 129.22, 128.92, 128.78, 127.26, 127.09, 83.36, 83.06, 80.81, 69.19, 68.90, 53.49, 49.97, 45.37, 43.60, 42.10, 41.32, 31.77, 31.69, 28.29, 14.55, 14.29 ppm.

MS: ESI: [M+H]+ m/z found 333.2, calculated 333.2 b) Preparation of Compound 33, tert-butyl 4-(pent-4-ynoyl)-2-((2-phenylacetamido)methyl)piperazine-1-carboxylate

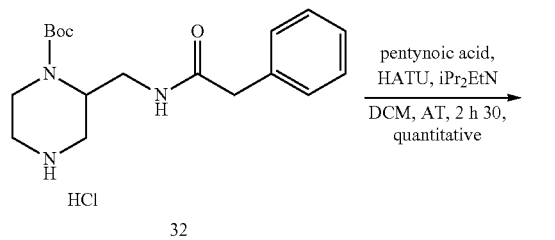

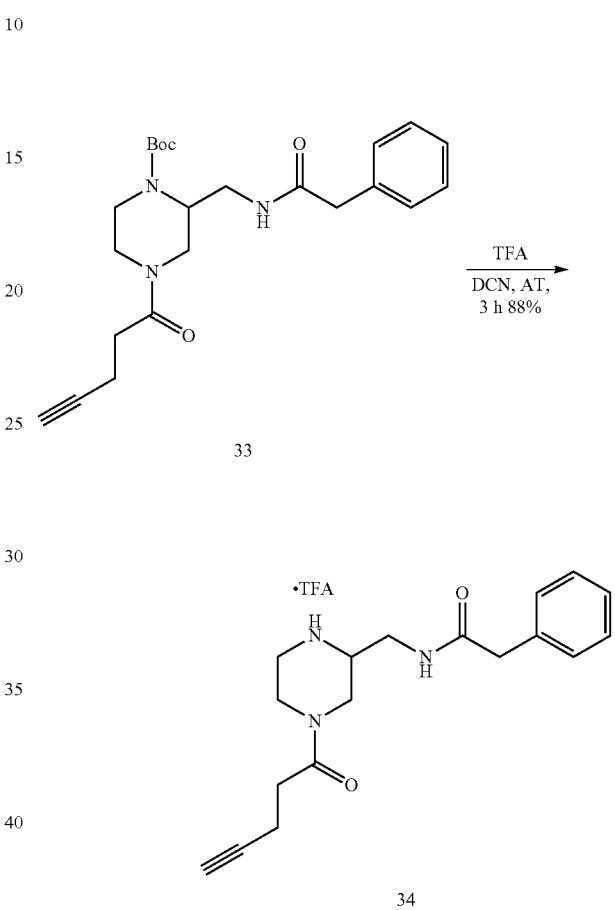

DIPEA (395 μL, 2.25 mmol, 2.2 eq) was added to a suspension, cooled to 0° C., of compound 32 (410 mg, 1.11 mmol, 1.0 eq), pentynoic acid (122 mg, 1.22 mmol, 1.1 eq) and HATU (473 mg, 1.22 mmol, 1.1 eq) in anhydrous DCM (30 mL) under an inert atmosphere of argon, and the reaction mixture was stirred at 0° C. for 15 min, then at AT for 2 h15. At the end of the reaction, the reaction mixture was diluted with DCM (20 mL) and washed twice with a saturated aqueous solution of NaHCO$_3$ (2×50 mL) and once with brine (50 mL). The organic phase was dried with Na$_2$SO$_4$, filtered and evaporated. The unrefined reaction medium was purified by column chromatography over neutral alumina (petroleum ether:ethyl acetate/15:85/v:v) in order to obtain the compound 33 in the form of a pale yellow solid (552 mg, yield: quantitative).

$^1$H-NMR (300 MHz, CDCl$_3$) δ=7.43-7.15 (m, 5H), 6.25 (s, 1H), 4.47-4.15 (m, 2H), 4.00-3.57 (m, 2.7H), 3.52 (d, J=2.9 Hz, 2H), 3.33 (m, 0.7H), 3.28-2.85 (m, 2.8H), 2.68-2.29 (m, 4.5H), 2.00 (d, J=8.4 Hz, 1H), 1.47 (s, 9H) ppm.

$^{13}$C-NMR (75 MHz, CDCl$_3$) δ=171.53, 171.33, 170.51, 170.26, 165.70, 154.91, 134.84, 129.22, 128.92, 128.78, 127.26, 127.09, 83.36, 83.06, 80.81, 69.19, 68.90, 53.49, 49.97, 45.37, 43.60, 42.10, 41.32, 31.77, 31.69, 28.29, 14.55, 14.29 ppm.

MS: ESI: [M+H]+ m/z found 413.3, calculated 413.2

R$_f$=0.29 (petroleum ether:ethyl acetate/2:8/v:v)

c) Preparation of Compound 34, N-((4-(pent-4-ynoyl)piperazin-2-yl)methyl)-2-phenylacetamide, in the Form of a Salt with Trifluoroacetic Acid The procedure used was the same as that described for the synthesis of compound 8, but using the compound 33 (550 mg, 1.33 mmol, 1.0 eq) in DCM (5 mL) and TFA (5 mL) in order to provide the compound 34 in the form of a white powder (500 mg, 1.17 mmol yield: 88%).

$^1$H-NMR (500 MHz, MeOD) δ=7.33-7.22 (m, 4H), 7.22-7.15 (m, 1H), 4.45 (t, J=13.4 Hz, 1H), 3.97 (t, J=13.4 Hz, 1H), 3.45-3.11 (m, 6.5H), 3.06 (t, J=10.6 Hz, 0.5H), 3.01-2.81 (m, 2H), 2.67-2.46 (m, 2H), 2.42 (m, 2H), 2.24 (d, J=1.6 Hz, 1H), 1.34-1.26 (m, 1H) ppm.

$^{13}$C-NMR (125 MHz, MeOD) δ=175.33, 172.22, 172.09, 163.50, 163.23, 162.96, 162.68, 136.48, 136.39, 130.30, 130.27, 130.17, 129.70, 129.65, 128.09, 128.03, 83.85, 70.32, 70.26, 56.37, 56.22, 55.75, 54.81, 46.53, 44.58, 44.48, 43.72, 43.66, 43.55, 43.26, 42.64, 40.34, 40.19, 40.08, 39.63, 39.42, 32.73, 32.59, 18.65, 15.11, 13.09 ppm.

MS: ESI: [M+H]+ m/z found 313.2, calculated 313.2

XII—Preparation of Compound 36, 4-nitrophenyl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

EXAMPLE 5 a) Preparation of Compound 35, 4-nitrophenyl 4-(pent-4-ynoyl)-2-((2-phenylacetamido)methyl)piperazine-1-carboxylate

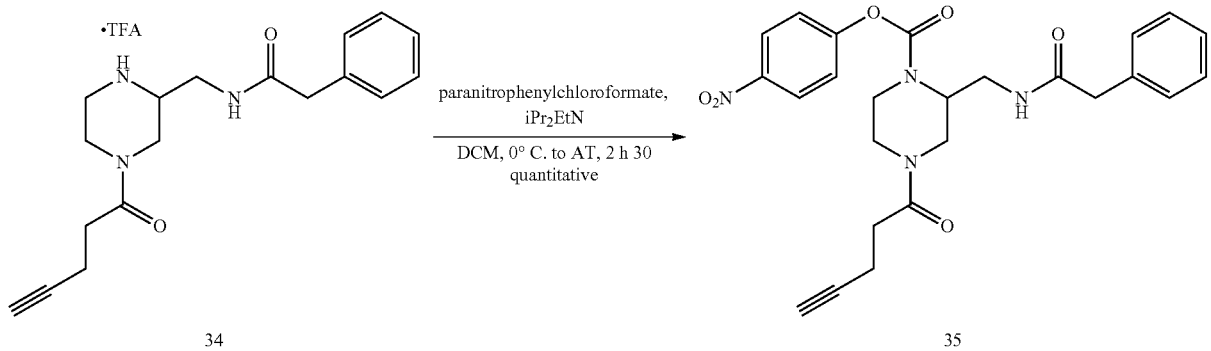 [SMILES: C#CCCC(=O)N1CCNC(CNC(=O)Cc2ccccc2)C1 ; C#CCCC(=O)N1CCN(C(=O)Oc2ccc([N+](=O)[O-])cc2)C(CNC(=O)Cc2ccccc2)C1]

Para-nitrophenolchloroformate (28 mg, 0.130 mmol, 1.1 eq) was added all at once to a solution, cooled to 0° C. and under an inert atmosphere of argon, of compound 34 (50 mg, 0.117 mmol, 1.0 eq) and DIPEA (55 µL, 0.30 mmol, 2.5 eq) in anhydrous DCM (2 mL). The reaction mixture was stirred at 0° C. for 30 min then at AT for 2 h. At the end of the reaction, the reaction mixture was diluted with DCM (20 mL) and washed twice with a saturated aqueous solution of NaHCO$_3$ (2×25 mL) and once with brine (25 mL). The organic phase was dried with Na$_2$SO$_4$, filtered and evaporated. The unrefined reaction medium was purified using silica gel column chromatography (petroleum ether:ethyl acetate/2:8/v:v) in order to obtain the compound 35 in the form of a colorless solid (60 mg, yield: quantitative).

$^1$H-NMR (500 MHz, CDCl$_3$) δ=8.15 (t, J=9.8 Hz, 2H), 7.33-7.01 (m, 7H), 6.23 (s, 0.4H), 6.08-5.82 (m, 0.6H), 4.60-4.36 (m, 1.5H), 4.32-4.17 (m, 0.5H), 4.05-3.88 (m, 1.4H), 3.84 (m, 0.8H), 3.77-3.62 (m, 0.8H), 3.62-3.16 (m, 4.5H), 3.12 (t, J=12.0 Hz, 0.5H), 2.96-2.65 (m, 1.8H), 2.65-2.26 (m, 4.2H), 2.08-1.86 (m, 1.5H), 1.29-1.13 (m, 0.5H) ppm.

$^{13}$C-NMR (125 MHz, CDCl$_3$) δ=171.59, 171.35, 170.80, 170.40, 170.28, 155.85, 152.84, 152.40, 145.05, 144.94, 134.69, 134.48, 129.35, 129.25, 129.08, 128.96, 127.50, 127.33, 125.17, 122.27, 122.13, 121.85, 83.28, 83.03, 69.37, 69.10, 53.54, 51.50, 51.25, 45.58, 45.23, 45.03, 43.68, 42.43, 42.09, 41.20, 40.59, 40.18, 38.70, 38.10, 37.48, 31.86, 31.75, 14.71, 14.40 ppm.

MS: ESI: [M+H]$^+$ m/z found 478.3, calculated 478.3
R$_f$=0.32 (petroleum ether:ethyl acetate/2:8/v:v)

b) Preparation of Compound 36, 4-nitrophenyl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

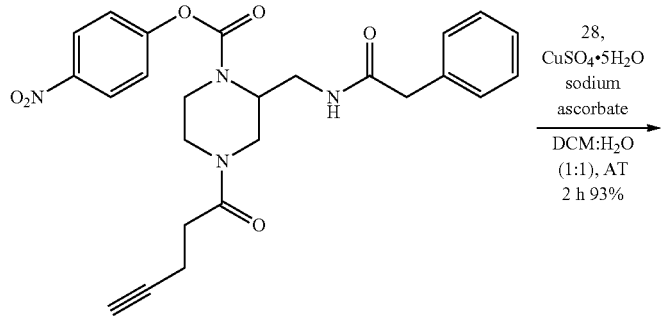

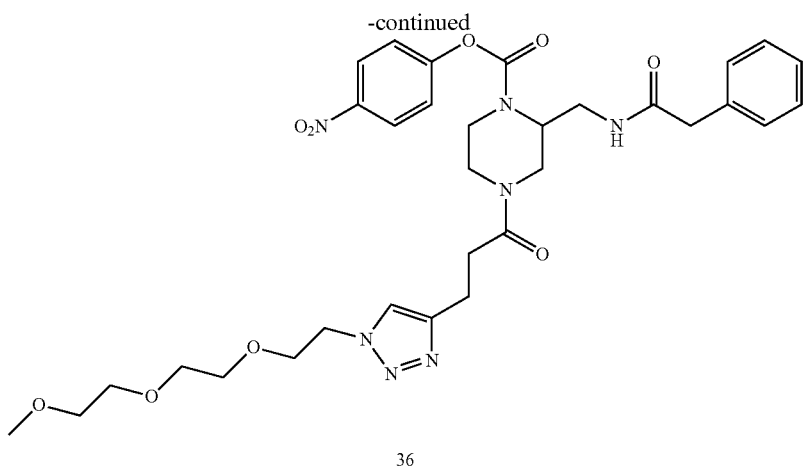

36

The procedure used was the same as that described for the synthesis of compound 31, with compound 35 (30 mg, 0.063 mmol, 1.0 eq), compound 28 (26 mg, 0.138 mmol, 2.2 eq), CuSO$_4$.5H$_2$O (9 mg, 0.04 mmol, 0.6 eq) and sodium ascorbate (16 mg, 0.08 mmol, 1.2 eq) in a mixture of DCM (1 mL) and water (1 mL). Following purification, compound 36 was obtained in the form of a pale yellow oil (39 mg, 0.058 mmol, yield: 93%).

$^1$H-NMR (500 MHz, CDCl$_3$) δ=8.29-8.01 (m, 2H), 7.54-7.01 (m, 7H), 4.56-4.24 (m, 5H), 4.05-3.66 (m, 5H), 3.66-3.37 (m, 12H), 3.31 (d, J=4.7 Hz, 3H), 3.25-2.55 (m, 7H), 2.18-1.84 (m, 1H) ppm.

$^{13}$C-NMR (125 MHz, CDCl$_3$) δ=172.78, 171.62, 156.11, 155.95, 152.46, 145.10, 144.97, 135.45, 134.92, 129.38, 128.97, 128.80, 127.31, 127.10, 125.18, 122.21, 72.00, 70.64, 70.60, 69.43, 59.14, 51.47, 51.26, 50.69, 50.44, 50.18, 45.45, 45.20, 44.63, 44.03, 43.80, 42.40, 42.09, 41.06, 40.63, 40.25, 40.10, 39.39, 38.05, 37.72, 37.48, 31.85, 31.39, 30.40, 29.77, 29.51, 28.59, 26.99, 21.36, 20.53 ppm.

MS: ESI: [M+H]$^+$ m/z found 667.3, calculated 667.3
R$_f$=0.31 (DCM:MeOH/95:5/v:v)

XIII-Preparation of Compound 39, 4-chloro-2-(6-chloro-4-oxo-3,4-dihydroquinazolin-2-yl)phenyl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

EXAMPLE 6 a) Preparation of Compound 38, 4-chloro-2-(6-chloro-4-oxo-3,4-dihydroquinazolin-2-yl)phenyl 4-(pent-4-ynoyl)-2-((2-phenylacetamido)methyl)piperazine-1-carboxylate

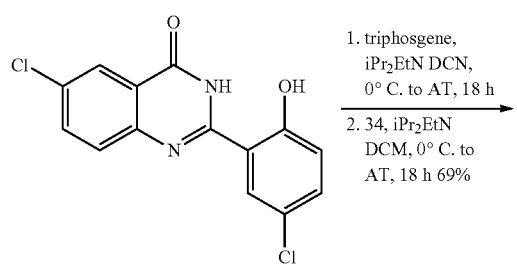

37

1. triphosgene, iPr$_2$EtN DCN, 0° C. to AT, 18 h
2. 34, iPr$_2$EtN DCM, 0° C. to AT, 18 h 69%

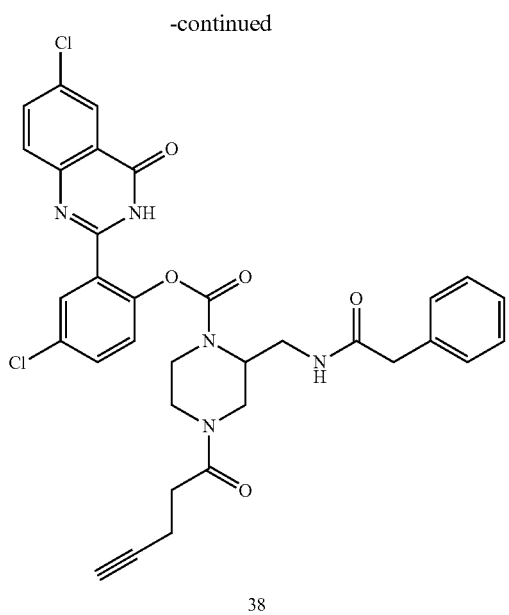

38

A solution of triphosgene (130 mg, 0.43 mmol, 3.3 eq) in anhydrous DCM (2 mL) followed by DIPEA (80 μL, 0.43 mmol, 3.3 eq) was added to a suspension, cooled to 0° C. and under an inert atmosphere of argon, of compound 37 (40 mg, 0.13 mmol, 1.1 eq) in anhydrous DCM (5 mL). This reaction mixture was stirred at 0° C. for 30 min then at AT for 18 h. The volatile compounds were then removed by evaporation under reduced pressure and the resulting solid was taken up in anhydrous DCM (5 mL). A solution of compound 34 (50 mg, 0.117 mmol, 1.0 eq) in anhydrous DCM (2 mL), followed by DIPEA (85 μL, 0.47 mmol, 4.0 eq) was added to this new suspension, and this reaction mixture was stirred at AT for 18 h. At the end of the reaction, the reaction mixture was diluted with DCM (20 mL) and washed twice with a saturated aqueous solution of NaHCO$_3$ (2×25 mL) and once with brine (25 mL). The organic phase was dried with Na$_2$SO$_4$, filtered and evaporated. The unrefined reaction medium was purified using two successive silica gel chromatographic columns (petroleum ether:ethyl acetate/2:8/v:v; and DCM:MeOH gradient of/99:1, 98:2, 97:3/v:v) in order to obtain the compound 38 in the form of a white solid (52 mg, 0.080 mmol, yield: 69%).

$^1$H-NMR (500 MHz, CDCl$_3$) δ=11.12-10.16 (m, 0.8H), 8.14 (s, 0.7H), 8.01-7.70 (m, 0.9H), 7.64 (s, 1.5H), 7.41 (s, 0.9H), 7.30-6.88 (m, 5.3H), 6.82-6.46 (m, 0.9H), 6.10 (s, 0.3H), 4.56-4.01 (m, 2H), 4.05-2.99 (m, 7.1H), 2.99-2.60 (m, 1.8H), 2.60-2.15 (m, 3.6H), 2.10-1.59 (m, 1.6H), 1.23 (m, 1.3H) ppm.

$^{13}$C-NMR (125 MHz, CDCl$_3$) δ=173.05, 171.80, 170.88, 170.50, 170.31, 161.41, 153.40, 153.05, 152.46, 149.57, 149.45, 147.43, 147.20, 147.09, 135.64, 135.41, 135.19, 134.83, 134.72, 134.55, 133.55, 133.39, 133.14, 132.11, 131.72, 130.88, 130.52, 130.29, 129.61, 129.43, 129.27, 129.20, 129.05, 128.85, 127.99, 127.66, 127.45, 127.20, 127.16, 125.96, 125.80, 124.81, 124.35, 124.16, 122.27, 122.06, 121.85, 83.37, 83.08, 82.95, 69.53, 69.39, 69.06, 68.97, 51.86, 51.67, 45.26, 45.09, 44.96, 43.58, 43.38, 42.44, 41.78, 41.11, 40.58, 40.37, 39.74, 39.33, 38.86, 38.41, 38.02, 31.76, 29.72, 14.68, 14.33 ppm.

MS: ESI: [M+H]$^+$ m/z found 645.3, calculated 645.2

R$_f$=0.19 (DCM:MeOH/97:3/v:v)

b) Preparation of Compound 39, 4-chloro-2-(6-chloro-4-oxo-3,4-dihydroquinazolin-2-yl)phenyl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate

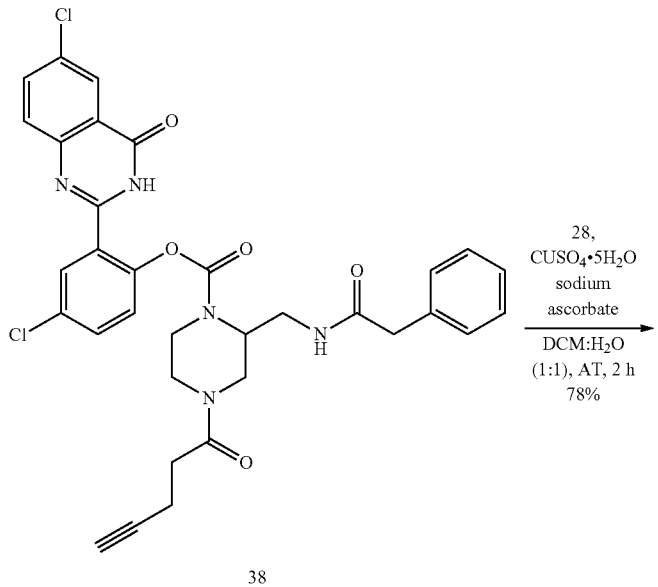

38

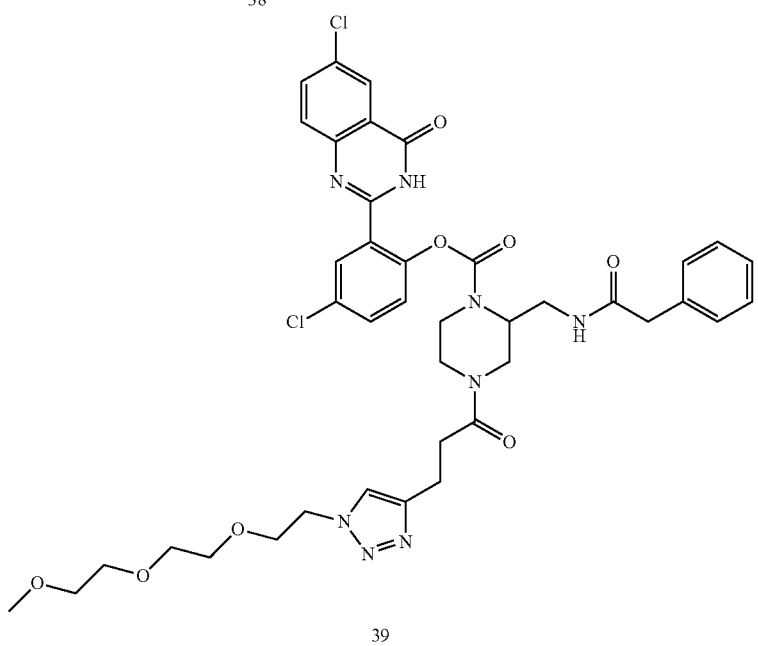

39

The procedure used was the same as that described for the synthesis of compound 31, with compound 38 (50 mg, 0.077 mmol, 1.0 eq), compound 28 (31 mg, 0.170 mmol, 2.2 eq), CuSO$_4$.5H$_2$O (12 mg, 0.05 mmol, 0.6 eq) and sodium ascorbate (20 mg, 0.10 mmol, 1.2 eq) in a mixture of DCM (2 mL) and water (2 mL). Following purification, compound 39 was obtained in the form of a pale yellow oil (50 mg, 0.060 mmol, yield: 78%).

$^1$H-NMR (500 MHz, CDCl$_3$) δ=11.12 (s, 0.4H), 10.89 (s, 0.2H), 10.14-9.90 (m, 0.2H), 8.33-7.94 (m, 2H), 7.91-7.71 (m, 2H), 7.70-7.48 (m, 1.5H), 7.43-7.32 (m, 2H), 7.30-7.12

(m, 3.5H), 4.54 (m, 4H), 3.93 (m, 4H), 3.77-3.50 (m, 10H), 3.45-2.72 (m, 10H), 2.39 (s, 0.5H), 1.66 (s, 3H) ppm.

$^{13}$C-NMR (125 MHz, CDCl$_3$) δ=174.00, 173.14, 172.10, 171.24, 161.27, 152.45, 152.24, 149.84, 149.71, 147.59, 147.54, 147.30, 147.19, 135.53, 135.30, 135.16, 135.11, 134.89, 133.08, 133.02, 132.14, 132.09, 131.98, 131.67, 131.54, 131.04, 129.79, 129.44, 129.35, 128.84, 128.78, 128.68, 127.64, 127.19, 126.97, 126.04, 125.83, 125.11, 124.32, 124.22, 122.54, 72.01, 70.64, 70.59, 70.43, 69.27, 59.15, 52.06, 51.86, 51.50, 50.90, 50.58, 45.62, 45.47, 45.38, 45.17, 44.54, 44.01, 43.88, 43.72, 43.53, 41.87, 41.17, 40.84, 40.42, 40.00, 39.20, 39.11, 38.30, 38.28, 30.34, 29.70, 29.43, 21.39, 20.64 ppm.

MS: ESI: [M+H]$^+$ m/z found 834.5, calculated 834.3

R$_f$=0.13 (DCM:MeOH/96:4/v:v)

B—Evaluation of Hydrosolubility of the Compounds

The hydrosolubility of the compounds was evaluated as a function of the presence or absence of precipitate in buffered solutions of the compounds in question at different concentrations. These solutions were prepared as follows: A known quantity of substance was dissolved in an appropriate volume of DMSO in order to obtain a clear stock solution in a concentration of 100 mM in DMSO (except with commercial AMC-leucine (denoted AMC-Leu), which produced a cloudy solution under these conditions and the concentration of the stock solution in DMSO had to be reduced to 50 mM). These stock solutions were then diluted in a commercial PBS buffer in order to obtain a range of final concentrations between 1 mM and 50 μM. A compound was declared to be insoluble if a precipitate appeared and persisted after dilution.

Table 2 below presents the results of these solubility tests.

TABLE 2

| | Concentrations Product | | | | |
|---|---|---|---|---|---|
| | 1 mM | 500 μM | 250 μM | 100 μM | 50 μM |
| 12 - Ex 1 | soluble | soluble | soluble | soluble | soluble |
| 15 comparative 1 | insoluble | insoluble | insoluble | insoluble | insoluble |
| 31 - Ex 4 | soluble | soluble | soluble | soluble | soluble |
| 36 - Ex 5 | soluble | soluble | soluble | soluble | soluble |
| 39 - Ex 6 | insoluble | insoluble | soluble | soluble | soluble |
| AMC-Leu | insoluble | insoluble | insoluble | insoluble | insoluble |
| 21 - Ex 2 | insoluble | insoluble | soluble | soluble | soluble |
| 22 - Ex 3 | soluble | soluble | soluble | soluble | soluble |
| 27 comparative 2 | insoluble | insoluble | insoluble | soluble | soluble |

Conclusions: In all of the presented cases, the compounds in accordance with the invention had better solubility in aqueous solution compared with a commercial substrate without a linker arm or compared with a substrate incorporating a linker arm described in the applications WO 2013/045854 and WO 2014/020285.

Enzymatic Activation:

Certain of the compounds were tested in order to evaluate the fluorescence detected from enzymatic activity.

A solution of PGA (penicillin G amidase from *Escherichia Coli*, Waterstone Tech.) in PBS buffer or a solution of lipase (lipase from *Candida Rugosa*, Sigma-Aldrich) in PBS buffer was added to a solution of probe in accordance with the invention in PBS in a 96-well plate (black for fluorescence or transparent for absorbance).

Final concentration of probe: between 10 μM and 50 μM

Final concentration of PGA: 5 U

Or final concentration of lipase: 4 U

The plate was then incubated at 37° C. and the fluorescence or the absorbance was recorded over time with a multi-plate reader (EnSpire, Perkin Elmer). The resulting graphs are of results in triplicate.

For 4-methylumbeliferone (compounds 12, 15, 31, 21 and 27): Fluorescence: $\lambda_{ex}$=370 nm, $\lambda_{em}$=445 nm.

For 6-chloro-2-(5-chloro-2-hydroxyphenyl)quinazolin-4(3H)-one (compound 39): fluorescence: $\lambda_{ex}$=365 nm, $\lambda_{em}$=530 nm.

For para-nitrophenolate (compound 36): Absorbance: $\lambda_{abs}$=405 nm.

The results are presented in the accompanying FIGS. 1 to 8.

The change in fluorescence following activation of compound 12 by PGA is shown in FIG. 1.

Figure 2:
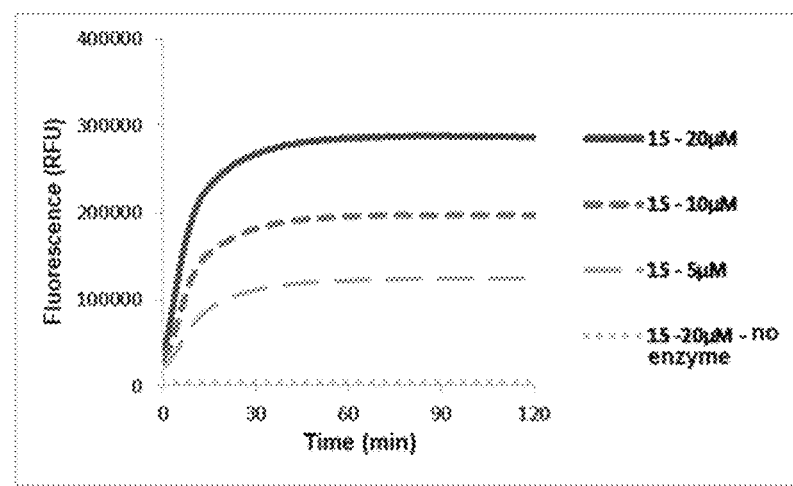

The change in fluorescence following activation of compound 15 by PGA is shown in FIG. 2.

Figure 3:
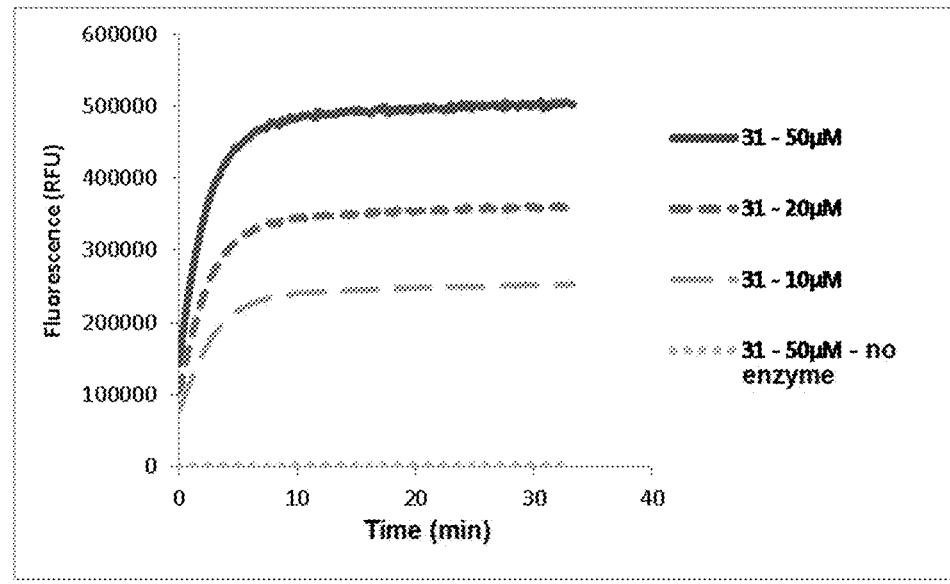

The change in fluorescence following activation of compound 31 by PGA is shown in FIG. 3.

Figure 4:
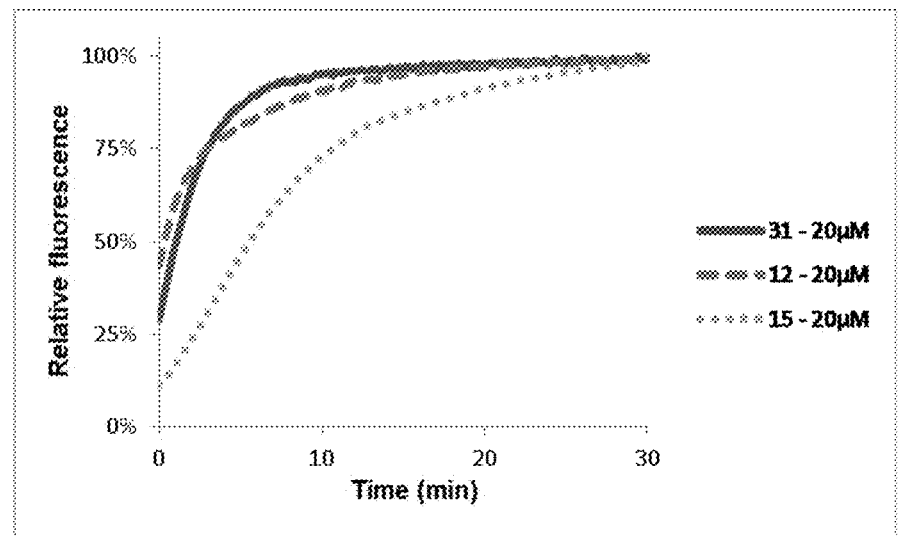

The comparison of the rates of response of compounds 12 and 31 in accordance with the invention, and of compound 15 used as a comparison following their activation by PGA is shown in FIG. 4.

Figure 5:
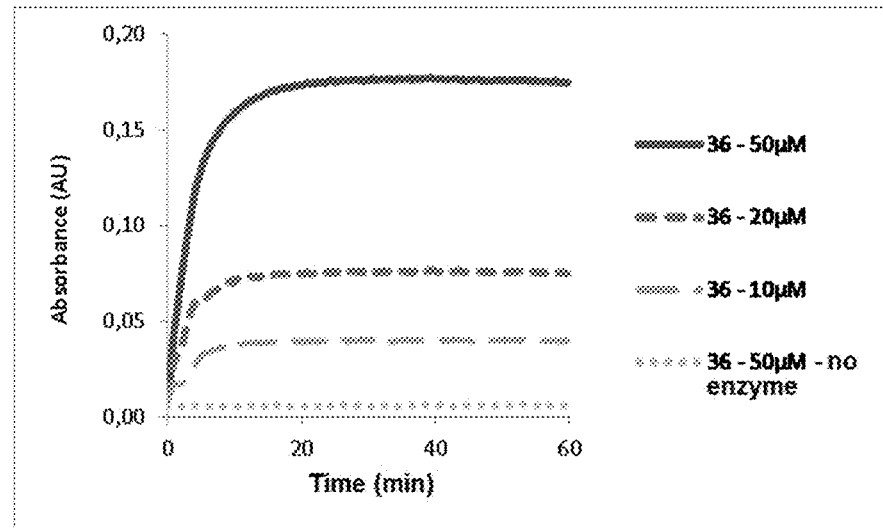

The change in absorbance following activation of compound 36 by PGA is shown in FIG. 5.

Figure 6:
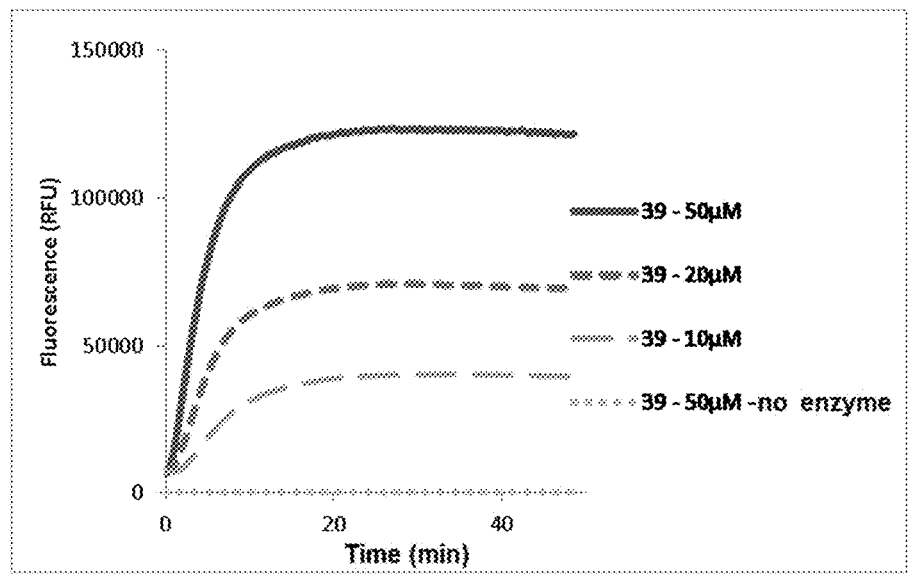

The change in fluorescence following activation of compound 39 by PGA is shown in FIG. 6.

Figure 7:
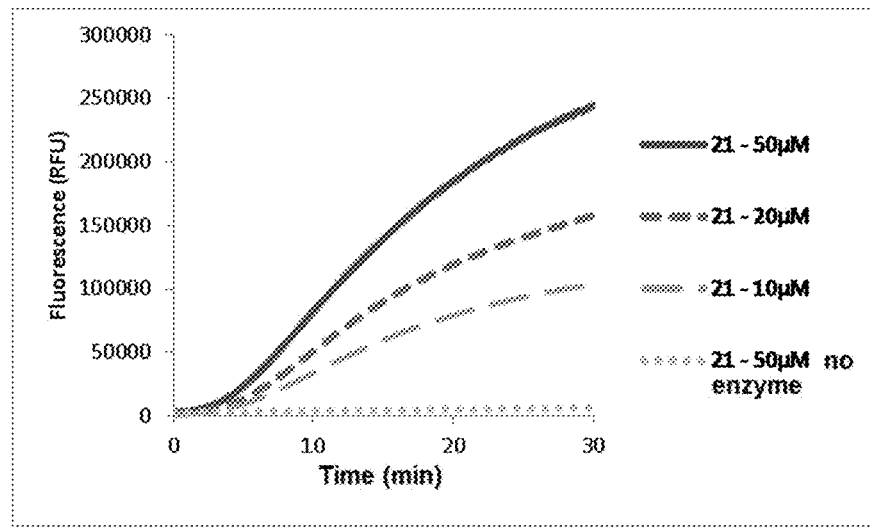

The change in fluorescence following activation of compound 21 by lipase is shown in FIG. 7.

Figure 8:
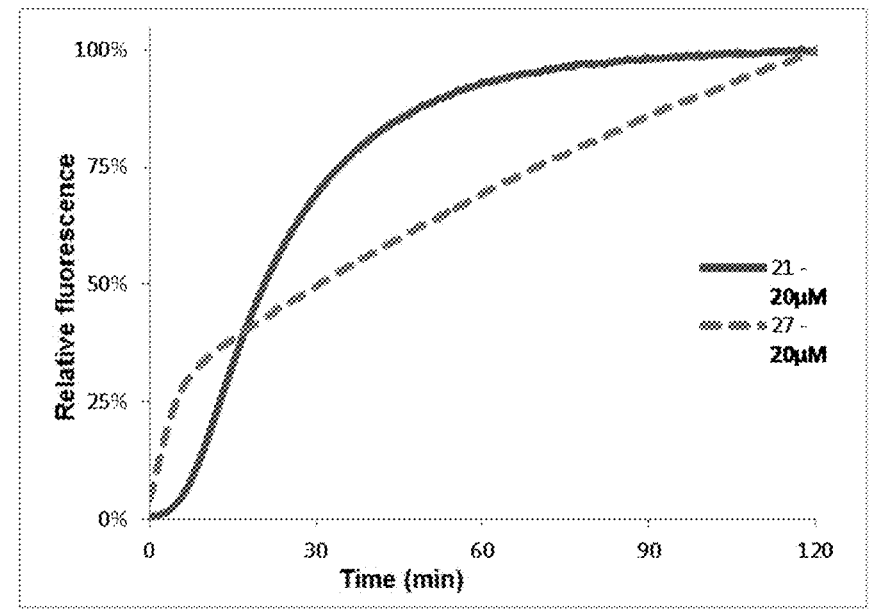

The comparison of the rates of response of compound 21 in accordance with the invention, and of compound 27 used as a comparison, following their activation by lipase is shown in FIG. 8.

Conclusions: the compounds in accordance with the invention can effectively be used to detect the presence of an enzymatic activity by means of fluorescence or absorbance measurements. Enzymatic recognition is still good despite incorporating a charge or a group that is relatively sterically hindered onto the linker arm.

The invention claimed is:

1. A probe with formula (I):

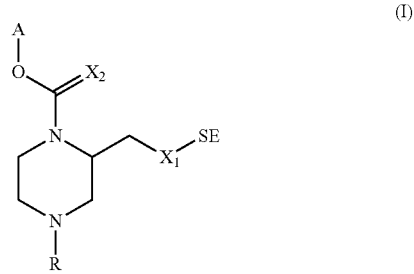

in which:

X$_2$=O or S;

either X$_1$ is an oxygen atom and SE is a glycosidase substrate or glucuronidase substrate and corresponds to a glycosyl group bonded to the remainder of the molecule via its anomeric carbon or SE is an esterase substrate and corresponds to a —C(O)Ri group in which Ri represents an alkyl group containing 1 to 20 carbon atoms, an alkenyl group containing 1 to 20 carbon atoms, a benzyl, aryl, or heteroaryl group;

or $X_1$ represents NH and SE is a protease or peptidase substrate and corresponds to a peptidyl group bonded to the remainder of the molecule via an acyl function carried by its terminal carbon or by a side chain; and A is a chromophore or fluorophore moiety having an aromatic group comprising one or more aromatic rings that may optionally be substituted, said rings possibly comprising one or more heteroatoms selected from nitrogen, oxygen, or sulfur atoms and/or one or more carbon atoms in the form of a carbonyl, C=O;

R represents a hydrogen atom or -(L)n-GP, with n equal to 0 or 1;

L is a linker arm; and

GP is a hydrosolubizing group selected among the group consisting in function F1, function F2, groups comprising one or more functions F1 and/or F2, polyethylene glycols, sugars, polysaccharides, and peptide groups;

F1 is selected among the group consisting of amines (primary, secondary, or tertiary), amidine, guanidine, and tetrazole; and F2 is selected among the group consisting of carboxylate, sulfonate, and phosphate; as well as their physiologically acceptable salts.

2. The probe according to claim 1, wherein A is an aromatic compound selected from para-nitrophenol and its derivatives, indigoids, cyclohexenoesculetin, alizarin and hydroxyflavone.

3. The probe according to claim 1, wherein A is an aromatic compound in which —OA is selected from:

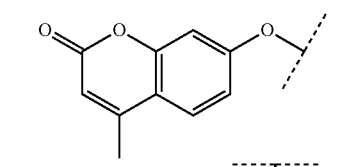

umbelliferone

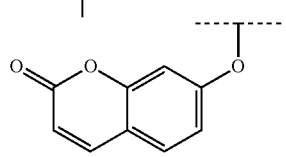

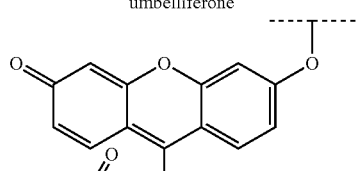

fluorescein

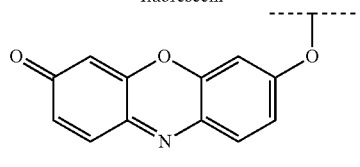

resorufin

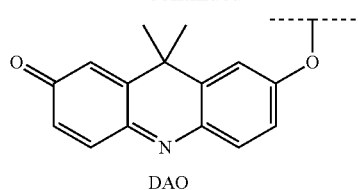

DAO

4. The probe according to claim 1, wherein A is an aromatic compound in which —OA has the formula (AA):

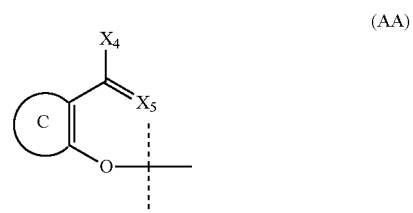

(AA)

in which:
either $X_5$ is an oxygen atom and $X_4$ is a —$NH_2$, —OH, —SH, alkyl, aryl, —O-alkyl, —O—phenyl, —NH-alkyl, —NH-phenyl, —S-alkyl, or —S-aryl group, said alkyl and phenyl groups possibly being substituted or unsubstituted; or $X_5$ represents a nitrogen atom and is bonded to $X_4$, which then represents CH, O, S, N, or NH in order to form a substituted or unsubstituted heteroaryl; and

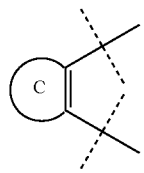

represents an aryl or a heteroaryl, which may be substituted or unsubstituted selected from phenyl and naphthyl groups, and:

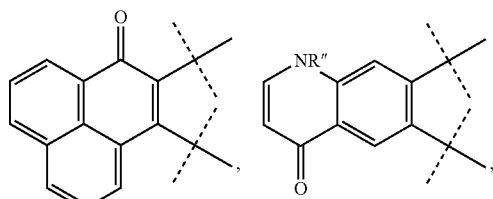

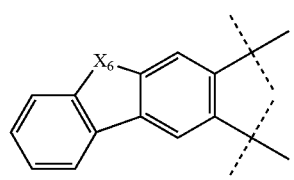

said groups possibly being substituted or unsubstituted;
in which $X_6$ represents S, O, or NR", and R" represents a hydrogen atom or a ($C_1$-$C_4$) alkyl group;

—OA is phenoxy in type and corresponds to the following structures (BB) or (CC):

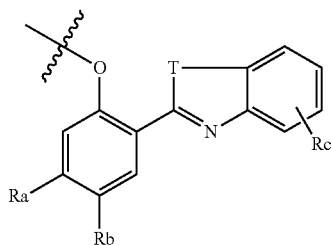

(BB)

in which
T is —NH—C(O)—, —S—, —O—, —NH, N-alkyl, or N-aryl;
Ra is hydrogen or an electron-attracting carbon-containing substituent such as —CN or —COORd, in which Rd represents a $(C_1-C_4)$alkyl group, or Ra is —CONReRf, in which Re and Rf, which may be identical or different, represent hydrogen or a $(C_1-C_4)$alkyl group, or Ra is —CF$_3$ or a 2-oxazolyl, 2-thiazolyl, 2-imidazolyl, 2-benzoimidazolyl, 4-pyrimidinon-2-yl, or quinazolinon-2-yl group;
Rb is hydrogen, a chlorine, bromine, iodine, or fluorine atom, —OH, —NH$_2$, —NRgRh, —NHRg, or —ORg, in which Rg and Rh each independently represent a $(C_1-C_4)$alkyl;
or Ra and Rb are bonded together to form a hydrocarbon chain comprising 4 or 5 links, which may be saturated or unsaturated, substituted or unsubstituted, optionally interrupted by one or more heteroatoms selected from N, S, and O;
Rc is hydrogen, Br, Cl, I, or F;

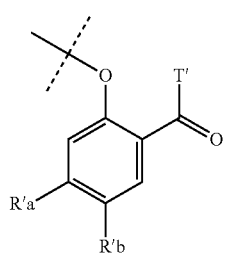

(CC)

in which:
T' is NH$_2$, OH, an aryl group, a $(C_1-C_4)$alkyl group, SH, NHR'c, OR'c, NR'cR'd, or SR'c group, in which R'c and R'd, which may be identical or different, represent a $(C_1-C_4)$ alkyl or aryl group;
R'a is hydrogen or an electron-attracting carbon-containing substituent such as —CN, or —COOR'e, in which R'e represents a $(C_1-C_4)$alkyl group, or R'a is —CONR'fR'g, in which R'f and R'g, which may be identical or different, represent hydrogen or a $(C_1-C_4)$alkyl group, or R'a is —CF$_3$ or a 2-oxazolyl, 2-thiazolyl, 2-imidazolyl, 2-benzoimidazolyl, 4-pyrimidinon-2-yl, or quinazolinon-2-yl;
R'b is hydrogen, a chlorine, bromine, iodine, or fluorine atom, —OH, —NH$_2$, —NR'hR'i, or —OR'h, in which R'h and R'i, which may be identical or different, represent a $(C_1-C_4)$alkyl group;
or R'a and R'b are bonded together to form a hydrocarbon chain comprising 4 or 5 links, which may be saturated or unsaturated, substituted or unsubstituted, optionally interrupted by one or more heteroatoms selected from N, S, and O.

5. The probe according to claim 1, wherein A is an aromatic compound in which —OA has one of the following formulas:

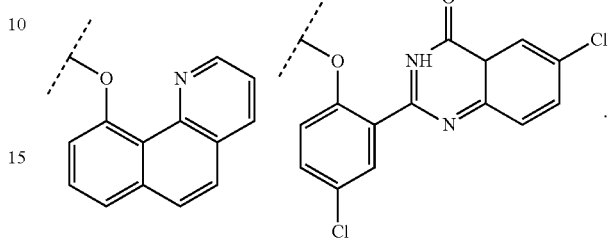

6. The probe according to claim 1, wherein R represents -(L)n-GP in which n =1 and L is a -(L1)m1-(L2)m2-(L'1)m'1- arm, defined in the direction piperazine ->group GP, in which:
L1 and L'1, which may be identical or different, are selected from —O—, —NH—, —N($C_{1-6}$)alkyl-, —N(phenyl)-, —N(aryl)-, —C(O)—, —C(O)O—, —OC(O)—, —OC(O)—O—, —NHC(O)—O—, —OC(O)—NH—, —NHC(O)—NH—, —S—, —SO$_2$-, —N═N—, —NHC(O)—, and —CONH—;
L2 is selected from the following bivalent groups: $(C_{1-20})$alkyl, $(C_{1-20})$alkenyl, $(C_{1-20})$alkynyl, $(C_{6-24})$aryl, $(C_{7-44})$alkylaryl, $(C_{7-44})$alkenylaryl, $(C_{7-44})$alkynylaryl, $(C_{7-44})$alkylcycloalkyl, $(C_{7-44})$alkenylcycloalkyl, $(C_{7-44})$alkynylcycloalkyl, $(C_{7-44})$alkylheterocycloalkyl, $(C_{7-44})$alkenylheterocycloalkyl, $(C_{7-44})$alkynylheterocycloalkyl; said groups possibly being interrupted by or terminating in a triazole group and possibly being unsubstituted or substituted with one or more substituents selected from $(C_{1-10})$alkoxy, $(C_{1-10})$alkyl, $(C_{6-10})$aryl, amido, imido, phosphido, nitrido, $(C_{1-10})$alkenyl, $(C_{1-10})$alkynyl and —OH;
m1, m'1 and m2, which may be identical or different, are equal to 0 or 1; and
GP is as defined in claim 1.

7. The probe according to claim 6, wherein L represents -(L1)m1-(L2)m2-(L'1)m'1 in which L1═—C(O)—, m1=m2=1, m'1=1 or 0, and L2 and L'1 are as defined in claim 6.

8. The probe according to claim 1, wherein X$_2$ is an oxygen atom.

9. The probe according to claim 1, wherein:
X$_2$ is an oxygen atom;
either X$_1$ is an oxygen atom and SE is a glycosidase substrate or glucuronidase substrate and corresponds to a glycosyl group bonded to the remainder of the molecule via its anomeric carbon or SE is an esterase substrate and corresponds to a —C(O)Ri group in which Ri represents an alkyl group containing 1 to 20 carbon atoms, an alkenyl group containing 1 to 20 carbon atoms, a benzyl, aryl, or heteroaryl group;
or X$_1$ represents NH and SE is a protease or peptidase substrate and corresponds to a peptidyl group bonded to the remainder of the molecule via an acyl function carried by its terminal carbon or by a side chain; and R represents -L-GP, in which:
L represents -(L1)m1-(L2)m2-(L'1)m'1 in which L1=—C(O)—, m1=m2=1, m'1=1 or 0 and L2 and L'1 are as defined in claim 6; and
GP represents a function F₁ selected from ammonium, carboxylate, sulfonate and phosphate functions and from polyethylene glycols.

10. The probe according to claim 1, selected from:
4-methyl-2-oxo-2H-chromen-7-yl 2-((2-phenylacetamido)methyl)piperazine-1-carboxylate hydrochloride (compound 12):

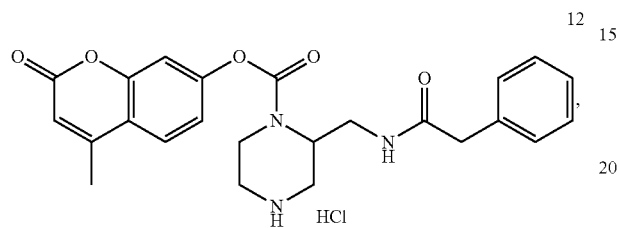

4-methyl-2-oxo-2H-chromen-7-yl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate (compound 31)

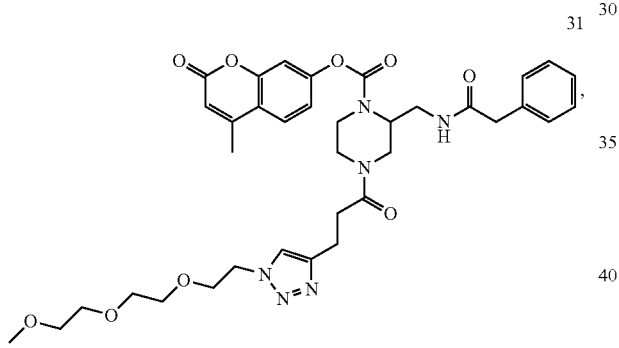

4-nitrophenyl 4-(3-(1-(2-(2-(2-methoxyethoxy)ethoxy)ethyl)- 1H-1,2,3-triazol-4-yl)propanoyl)-2-((2-phenylacetamido)methyl)piperazine-1-carboxylate (compound 36)

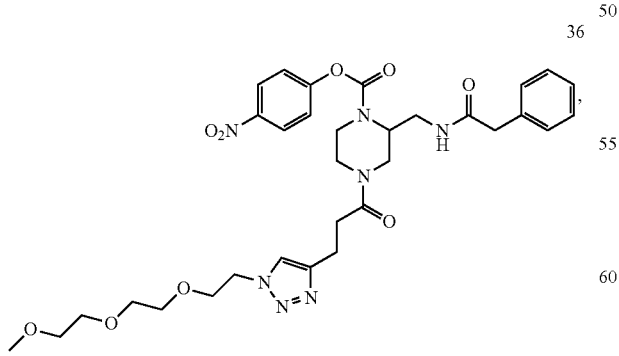

and
4-chloro-2-(6-chloro-4-oxo-3,4-dihydroquinazolin-2-yl)phenyl 4-(3-(1-(2-(2-(2-methoxyethoxy)ethoxy)ethyl)-1H-1,2,3-triazol-4-yl)propanoyl)-2-((2-phenylacetamido)methyl)piperazine-1-carboxylate (compound 39)

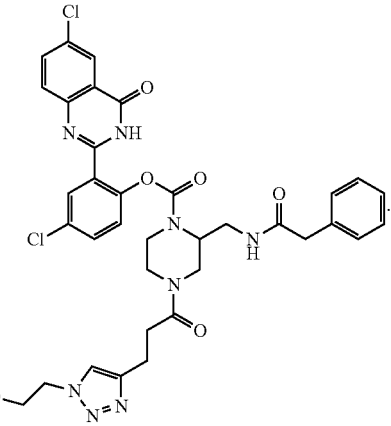

11. An intermediate compound with formula:

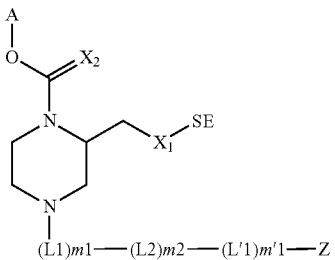

or

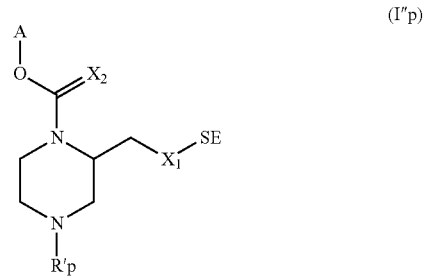

in which:
A, X₁, X₂, SE, L1, L'1, L2, m1, m'1, and m2 are as defined for (I) in claims 1;
Z represents C≡CH, N3, a N-oxysuccinimide or maleimide function; and
R'p represents a protective group for the amine functions selected from benzyl groups, —C(O)OR'₁ groups in which R'₁ represents an alkyl or alkenyl group containing 1 to 12 carbon atoms or a —(CH₂)$_{m3}$R"₁ group with R"₁ representing an aryl, cycloalkyl, or fluorenyl group and m3 is equal to 0, 1, 2, or 3, such as the carbobenzyloxy, ter-butyloxycarbonyl, 9-fluorenylmethyloxycarbonyl, and allyloxycarbonyl groups; as well as their salts.

12. The probe according to claim 1, wherein SE is —C(O)Ri in which Ri represents a benzyl, aryl or heteroaryl group.

13. The probe according to claim 1, selected from:

4-methyl-2-oxo-2H-chromen-7-yl2-((octanoyloxy)methyl)piperazine-1-carboxylate hydrochloride (compound 21)

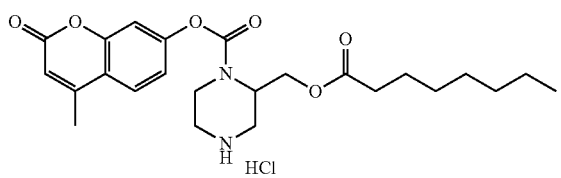

and 4-(4-(((4-methyl-2-oxo-2H-chromen-7-yl)oxy)carbonyl)-3-((octanoyloxy)methyl)piperazin-1-yl)butane-1-sulfonic acid (compound 22)

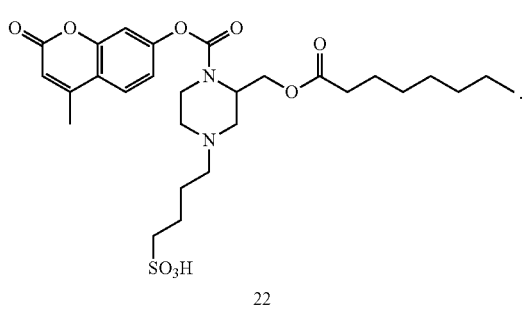

* * * * *